US012673202B2

(12) United States Patent
Robinson et al.

(10) Patent No.: US 12,673,202 B2
(45) Date of Patent: Jul. 7, 2026

(54) CORTICAL SUBARACHNOID AND INTRA VENTRICULAR BRAIN INTERFACES

(71) Applicants: William Marsh Rice University, Houston, TX (US); The Board of Regents of The University of Texas System, Austin, TX (US)

(72) Inventors: Jacob T. Robinson, Houston, TX (US); Peter Kan, Houston, TX (US); Joshua Chen, Houston, TX (US); Abdeali Dhuliyawalla, Houston, TX (US)

(73) Assignees: William Marsh Rice University, Houston, TX (US); The Board of Regents of The University of Texas System, Austin, TX (US)

( * ) Notice: Subject to any disclaimer, the term of this patent is extended or adjusted under 35 U.S.C. 154(b) by 244 days.

(21) Appl. No.: 18/658,986

(22) Filed: May 8, 2024

(65) Prior Publication Data

US 2024/0374893 A1     Nov. 14, 2024

Related U.S. Application Data

(60) Provisional application No. 63/465,041, filed on May 9, 2023.

(51) Int. Cl.
| | |
|---|---|
| *A61N 1/05* | (2006.01) |
| *A61M 25/00* | (2006.01) |
| *A61N 1/36* | (2006.01) |

(52) U.S. Cl.
CPC ......... *A61N 1/0551* (2013.01); *A61N 1/0529* (2013.01); *A61N 1/0531* (2013.01);
(Continued)

(58) Field of Classification Search
CPC .. A61N 1/0551; A61N 1/0529; A61N 1/0531; A61N 1/0534; A61N 1/36062; A61M 2025/0042
See application file for complete search history.

(56) References Cited

U.S. PATENT DOCUMENTS

| | | | |
|---|---|---|---|
| 8,401,655 B2 * | 3/2013 | De Ridder | ......... A61N 1/36017 |
| | | | 607/45 |
| 12,268,876 B2 * | 4/2025 | Knudson | ............. A61N 1/0551 |

(Continued)

FOREIGN PATENT DOCUMENTS

| | | | | |
|---|---|---|---|---|
| WO | WO-2018038930 A1 * | 3/2018 | ........... | A61B 5/6852 |
| WO | WO-2022226606 A1 * | 11/2022 | ............. | A61B 5/686 |
| WO | WO-2025235943 A1 * | 11/2025 | ............. | A61M 25/10 |

OTHER PUBLICATIONS

Chen et al., "A wireless millimetric magnetoelectric implant for the endovascular stimulation of peripheral nerves," *Nat. Biomed. Eng.*, 6:706-716 (2022).

(Continued)

*Primary Examiner* — Ab Salam Alkassim, Jr.
(74) *Attorney, Agent, or Firm* — pH IP Law

(57) ABSTRACT

The present disclosure is directed to neural interface devices and methods that accesses the subarachnoid space to enable minimally invasive modulation and recording of neural structures. Exemplary embodiments may comprise an implantable pulse generator and a microelectrode catheter. In particular embodiments, the microelectrode catheter comprises one or more stimulating and recording electrodes. Exemplary embodiments may also include methods comprising performing a lumbar puncture to access the spinal subarachnoid space and advancing microcatheter through the spinal subarachnoid space.

16 Claims, 18 Drawing Sheets

(52) U.S. Cl.
CPC ....... *A61N 1/0534* (2013.01); *A61N 1/36062*
(2017.08); *A61M 2025/0042* (2013.01)

(56) References Cited

U.S. PATENT DOCUMENTS

| | | | | |
|---|---|---|---|---|
| 2003/0149450 | A1* | 8/2003 | Mayberg | A61N 1/36 607/3 |
| 2005/0119703 | A1* | 6/2005 | DiLorenzo | A61N 1/36082 607/45 |
| 2012/0046531 | A1* | 2/2012 | Hua | A61B 5/293 607/45 |
| 2014/0046419 | A1* | 2/2014 | Knudson | A61N 1/36067 607/117 |
| 2015/0088212 | A1* | 3/2015 | De Ridder | A61N 1/36096 607/2 |
| 2017/0136238 | A1* | 5/2017 | Hartig | A61N 1/36171 |
| 2019/0192852 | A1* | 6/2019 | De Ridder | A61N 1/0531 |
| 2019/0201684 | A1* | 7/2019 | Williams | A61N 1/36132 |
| 2021/0213279 | A1* | 7/2021 | Rapoport | A61B 5/24 |
| 2022/0202486 | A1* | 6/2022 | Morales | A61B 18/1492 |

OTHER PUBLICATIONS

Singer et al., "Magnetoelectric materials for miniature, wireless neural stimulation at therapeutic frequencies," *Neuron*, 107(4):631-643, 2020.
Singer et al., "Wireless Power Delivery Techniques for Miniature Implantable Bioelectronics," *Adv. Healthc. Mater.* 10, 2100664 (2021).
Yu et al., "MagNI: a magnetoelectrically powered and controlled wireless neurotimulating implant," *IEEE Transactions on Biomedical Circuits and Systems*, 14(6):1241-1252, 2020.
Zhu, "Methods of frequency tuning vibration based microgenerator," Dissertation, University of Southampton, 2009.

* cited by examiner

121    122

125                    120

CORTICAL SUBARACHNOID AND INTRA VENTRICULAR BRAIN INTERFACES

CROSS-REFERENCE TO RELATED APPLICATION

This application claims priority to U.S. Provisional Patent Application No. 63/465,041, filed on May 9, 2023, titled "CORTICAL SUBARACHNOID AND INTRAVEN-TRICULAR BRAIN INTERFACES", which is incorporated by reference in its entirety for all purposes.

STATEMENT REGARDING FEDERALLY SPONSORED RESEARCH AND DEVELOPMENT

This invention was made with government support under Grant No. 1828869 awarded by the National Science Foundation, Grant No. U18EB029353 awarded by the National Institutes of Health, and Grant No. FA8650-21-2-7119 awarded the Air Force Research Laboratory. The government has certain rights in the invention.

BACKGROUND

1. Field of the Disclosure

The present disclosure relates generally to neural interface devices and methods that access the subarachnoid space to enable minimally invasive modulation and recording of neural structures.

2. Background

Deep brain stimulators, cortical stimulators, and endovascular neural interfaces can provide benefits to patients but include surgical risk and extended patient recovery times. Such devices may also require the use of anti-coagulants, can be limited in implantation locations, and not easily removed. Minimally invasive neural interfaces can be used to diagnose, manage, and treat many disorders with substantially reduced risks of surgical complications. Endovascular neural interfaces implanted in the veins or arteries is one approach, but it requires prescriptions of anti-thrombotic medication and are likely not explantable after endothelialization. More critically, the approach is limited by the small size and location of blood vessels, such that many important cortical, subcortical, spinal targets cannot be reached.

Interest in neurotechnologies that interface with the central nervous system to diagnose and treat diseases is accelerating [1-4]. As these technologies mature, applications expand beyond simple therapeutics toward more targeted, personalized therapies, and even neural prosthetics enabled by brain machine interfaces (BMIs) [5-7]. A major barrier to entry for these technologies is the ability to interface with the nervous system in a minimally invasive manner which does not damage existing healthy tissue. For example, it is estimated that adoption of deep brain stimulation (DBS) for Parkinson's Disease (PD) is limited to only about 10% of patients because of the perceived invasiveness and risks associated with procedures such as stereotactic brain surgery required to place electrodes in the brain [8]. Traditional neural implants that interface with the central nervous system (CNS) often rely on penetrating electrodes to access deep brain structures and require invasive surgeries such as craniotomies and burr holes [9-11].

Recently, innovative surgical approaches via the circulatory system have enabled less invasive implantation of devices that can interface with the nervous system [12]. By inserting catheters through the jugular vein in sheep, somatosensory evoked potentials were measured through the superior sagittal sinus, and more recently, the safety and efficacy of this approach has been demonstrated in humans [12,13]. Additionally, flexible microfabricated electrodes have been developed to navigate sub-millimeter vessels in rodent models for acute neural recordings [14]. However, this method requires a regimen anti-thrombotic medications, and the endothelialization of vascular implants makes it challenging to explant any devices [15]. The tortuous nature of the vasculature and the small caliber of the blood vessels in the brain and spinal cord make it difficult for robust and chronic electrodes to navigate to end targets in the central nervous system, making most cortical, subcortical, deep structures, and spinal cord inaccessible.

Accordingly, a need exists for systems, devices and methods that allow faster patient recovery times and significantly lower the risk of surgery, obviate the need for the use of anti-coagulants, have access to more versatile locations, and are removable.

SUMMARY

Thus, in accordance with the present disclosure, there is provided a cortical subarachnoid and intraventricular brain interface device comprising an external transmitter, an implantable pulse generator and a microelectrode catheter. In certain embodiments the microelectrode catheter comprises stimulating and recording electrodes configured for implantation into a spinal and intracranial subarachnoid space and/or ventricles of a brain. In particular embodiments, the implantable pulse generator comprises a battery. In specific embodiments the microelectrode catheter is configured to be implanted either on the brain convexity or into the ventricular system of an animal. Certain embodiments further comprise an external field transmitter, and in particular embodiments the external field transmitter is configured to provide an alternating magnetic field powered by a field driver at 20 kHz-1 MHZ, which powers a magneto-electric film at its mechanical resonant frequency.

Exemplary embodiments of the present disclosure include a chronic endocisternal neural interface that approaches brain and spinal cord targets through inner and outer cerebral spinal fluid (CSF) spaces. These spaces surround the nervous system and lack the tortuosity of the circulatory system, giving us access to the entire brain convexity, deep brain structures within the ventricles, and the spinal cord from the spinal subarachnoid space. Combined with miniature magnetoelectric-powered bioelectronics, the entire wireless system is deployable through a percutaneous procedure. The flexible catheter electrodes can be freely navigated throughout the body from the spinal to cranial subarachnoid space, and from the cranial subarachnoid space to the ventricles.

Exemplary embodiments have been implemented in a large animal model demonstrating the ability to reposition the recording and stimulation electrodes or explant the neural interface after chronic implantation. This enables applications in therapies that require transient or permanent brain/machine interface such as stroke rehabilitation and epilepsy monitoring and opens a new class of minimally invasive endocisternal bioelectronics.

Exemplary embodiments include a cortical subarachnoid and intraventricular brain interface device comprising an implantable pulse generator and a microelectrode catheter, where the microelectrode catheter comprises stimulating and recording electrodes, and the stimulating and recording electrodes are configured for implantation into a spinal and intracranial subarachnoid space or for implantation into ventricles of a brain. In certain embodiments the implantable pulse generator comprises a battery. In particular embodiments the microelectrode catheter is configured to be implanted either on the brain convexity or into the ventricular system of an animal. Some embodiments further comprise an external transmitter for delivering data or energy to the implantable pulse generator. In specific embodiments the external field transmitter is configured to provide an alternating magnetic field powered by a field driver at 20 kHz-1 MHZ, which powers a magnetoelectric film at its mechanical resonant frequency.

In certain embodiments the implantable pulse generator is configured to generate stimulation amplitudes of at least 12.0 volts. In particular embodiments the implantable pulse generator is configured to generate a pulse width of approximately 250 µs. Specific embodiments further comprise a wireless communication device. In some embodiments the wireless communication device comprises a coil. In exemplary embodiments the wireless communication device is configured to transmit wireless signals to the implantable pulse generator and receive wireless signals from the implantable pulse generator.

In particular embodiments the wireless communication device is configured to communicate with the implantable pulse generator via a magnetoelectric backscatter protocol. In specific embodiments the implantable pulse generator comprises a magnetoelectric film. In particular embodiments the implantable pulse generator comprises a printed circuit board.

Exemplary embodiments include a method of implanting a cortical subarachnoid and intraventricular brain interface device, with the method comprising: performing a lumbar puncture to access the spinal subarachnoid space; advancing a microcatheter through the spinal subarachnoid space; and advancing the microcatheter through the craniocervical junction to access an intracranial subarachnoid space, leading to access to a brainstem, a base of a brain, and a brain convexity. In certain embodiments of the method, the microcatheter comprises a stimulating electrode and a recording electrode.

Exemplary embodiments include a method of implanting a cortical subarachnoid and intraventricular brain interface device, with the method comprising: performing a lumbar puncture to access the spinal subarachnoid space; advancing a microcatheter through the spinal subarachnoid space; advancing the microcatheter through the craniocervical junction to access a third ventricle; and accessing a thalamus, basal ganglia, and corpus callosum for stimulation and recording. In certain embodiments of the method, the third ventricle is accessed through either a floor of the third ventricle or through the fourth ventricle and the cerebral aqueduct.

Exemplary embodiments include a method of implanting a cortical subarachnoid and intraventricular brain interface device, with the method comprising: performing a lumbar puncture to access spinal subarachnoid space; advancing a microelectrode catheter through the spinal subarachnoid space; implanting one or more stimulating electrodes and recording electrodes into a spinal or intracranial subarachnoid space or into ventricles of a brain of a subject; implanting an implantable pulse generator into the subject; generating a stimulation signal via the implantable pulse generator; and recording a response signal from the subject via the one or more recording electrodes. Particular embodiments of the method further comprise transmitting the response signal via a magnetoelectric backscatter protocol. In certain embodiments of the method, the implantable pulse generator comprises a magnetoelectric film.

The inventors hypothesized that the ventricular system and subarachnoid space could provide an alternative that would allow increased access to the brain convexity and spinal cord and avoid the need for anti-thrombotic medication. Like the circulatory system, the ventricular system and subarachnoid space that holds 150 mL of cerebrospinal fluid (CSF) is tightly coupled with the CNS. The CSF has long been shown to play a crucial role in CNS homeostasis, ensuring mechanical protection, and enabling communication between the CNS and vascular system, lymphatic system, peripheral nervous system, and immune system [16]. CSF is primarily produced in the choroid plexi within the lateral, third and fourth ventricles. It then flows from the ventricular system to the cerebral and spinal surface (subarachnoid space) through the foramen of Luschka and Magendie and is reabsorbed into the dural venous sinus through arachnoid villi. Through this network, this space is in contact with major CNS therapeutic targets and BMI targets such as deep brain structures, brain cortex, and spinal cord. This is also a space familiar to patients and neurosurgeons as many disorders are currently treated using the CSF space and catheter technology (e.g. hydrocephalus, spasticity, and back pain) [17].

To fully take advantage of these minimally invasive surgical approaches, it is important to reduce the size of the bioelectronic implants. There has been significant progress in miniaturization by developing battery-free devices that rely on wireless power transfer. These techniques that use radio frequency, magnetic fields, and ultrasound enable implants to be miniaturized down to the millimeter scale and operated at centimeter depths within the body [18-27]. These millimeter scaled devices enable the system to also be fully implanted with a minimally invasive percutaneous procedure. Recently, there have been demonstrations of devices that interface with the CNS through CSF such as flexible microelectrodes implanted through surgical holes in the skull into the subarachnoid space [28,29]. Minimally invasive approaches involving implanting electrodes into the epidural space of the spinal column have also been explored [30]. However, the ability to deploy a full system that has access to multiple CNS sites such as brain and spinal cord simultaneously through a minimally invasive procedure and being able to wirelessly stimulate and record these neural structures over extended periods of time has not been reported previously.

Exemplary embodiments of the present disclosure include a minimally invasive endocisternal interface (ECI) that accesses multiple targets (cortical surface, deep brain structures, and spinal cord) through the ventricles and subarachnoid space. Exemplary embodiments also demonstrate simultaneous stimulation and recording from both the brain and spinal cord through a minimally invasive percutaneous lumbar puncture. In addition, the entire system can be implanted percutaneously by coupling the catheter electrode with a miniaturized implantable pulse generator using magnetoelectric (ME) wireless data and power transfer technology.

This disclosure presents a class of neural interface that accesses the subarachnoid space to enable minimally invasive modulation and recording of neural structures. One embodiment provides a cortical subarachnoid-ventricular neural interface. In exemplary embodiments, some variations are possible within the electrode interface of the device as well as the implanted pulse generator. For example, inductive coupling, near-infrared, ultrasound, and/or radio frequency (RF) can all be used to wirelessly power a battery-free implanted pulse generator (IPG). The neural interface can also instead include a battery-powered implanted pulse generator that could be wirelessly charged or be replaced with follow up surgeries. The existing microcatheter electrodes used could be replaced with fabricated flexible electrode meshes and electrode arrays to include a multi-channel interface within the cerebrospinal fluid (CSF) space. Different encapsulation technologies can be used depending on the wireless power used in the IPG. The geometry is not limited to our current iteration.

Embodiments of the present disclosure can be used for epilepsy monitoring and treatments to prevent seizures, to enable therapeutic neuromodulation, brain-computer interfaces, or stroke rehabilitation. There are many potential applications for this technology especially in deep brain stimulation because exemplary embodiments are able to access neural tissue without damaging and disturbing the native tissue like traditional penetrating electrodes. Furthermore, this method requires a single minimally invasive lumbar puncture to access the central nervous system allowing for applications in treatment of chronic pain with spinal cord stimulation or treatment of depression, Alzheimer's, Parkinson's, and OCD in the deep brain. Because exemplary embodiments are also capable of recording, they can also be applied to develop closed-loop neural interfaces or be used in neural prosthetic applications. Because this technology is removable, exemplary embodiments can also target acute neural dysfunctions. Exemplary embodiments are also capable of stimulating and recording neural activity for brain computer interfaces for potential neural prosthetic applications. Sensors can also be integrated into the system to allow for continuous monitoring of biomarkers such as biochemical markers in the CSF or intracranial pressure.

Exemplary embodiments of the present disclosure can be compared to deep brain stimulators, cortical stimulators, and endovascular neural interfaces. Embodiments of the present disclosure provide significant advantages over such devices. For example, embodiments of the present disclosure are minimally invasive in comparison to penetrating deep brain electrodes, which could allow faster patient recovery times and significantly lower the risk of surgery. In comparison to endovascular neural interfaces, exemplary embodiments of the present disclosure obviate the need for the use of anti-coagulants, have access to more versatile locations, and are removable. Closed-loop neural interfaces, implantable drug delivery, and chronic bioelectronic implants may incorporate embodiments of the present disclosure.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any system, device or method described herein can be implemented with respect to any other system, device or method described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
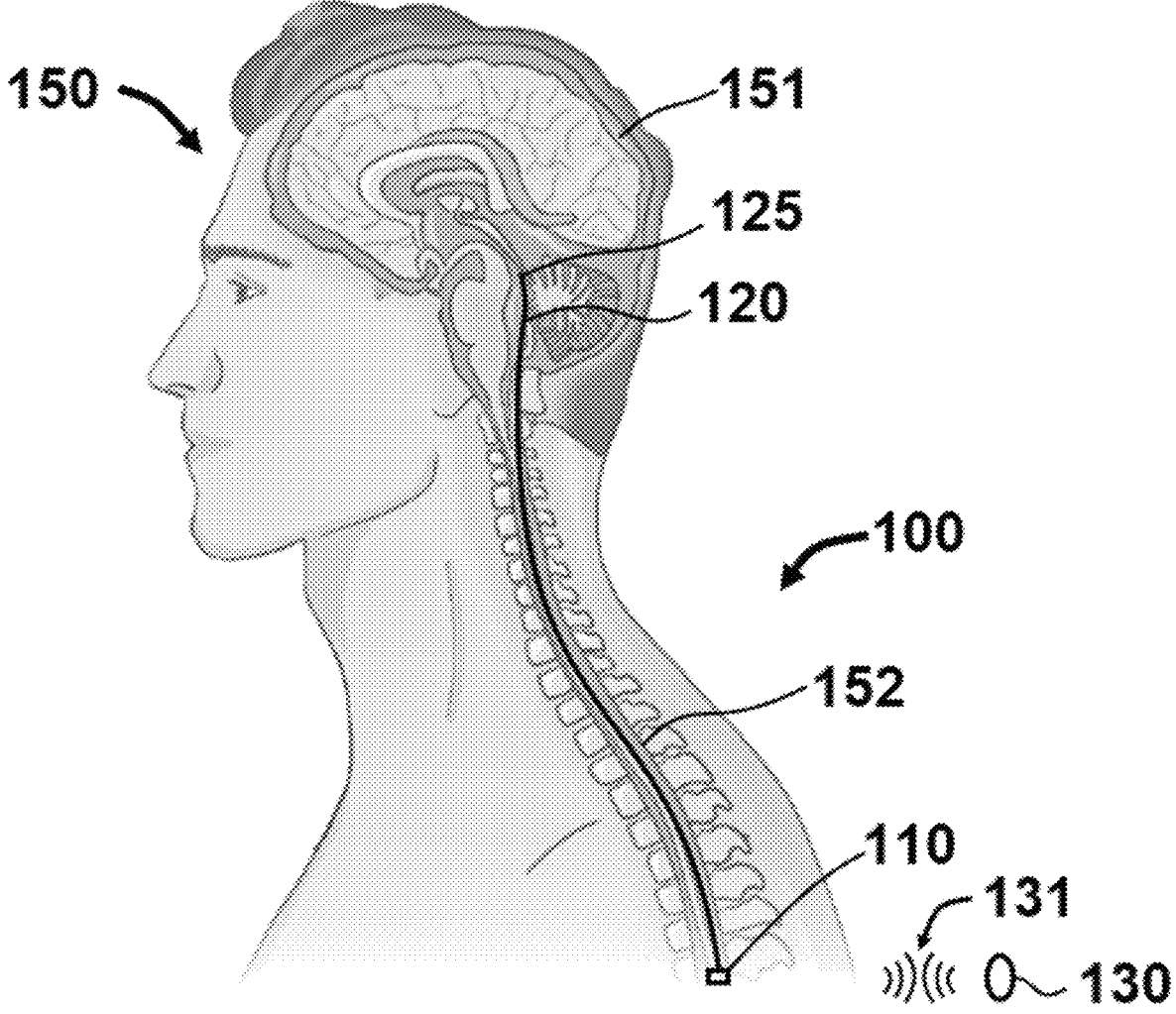
FIG. 1 illustrates a schematic section view of an embodiment according to the present disclosure implanted in a subject.
Figure 2:
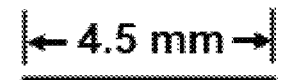
FIG. 2 illustrates a schematic view of a distal portion of the embodiment of FIG. 1.
Figure 3:
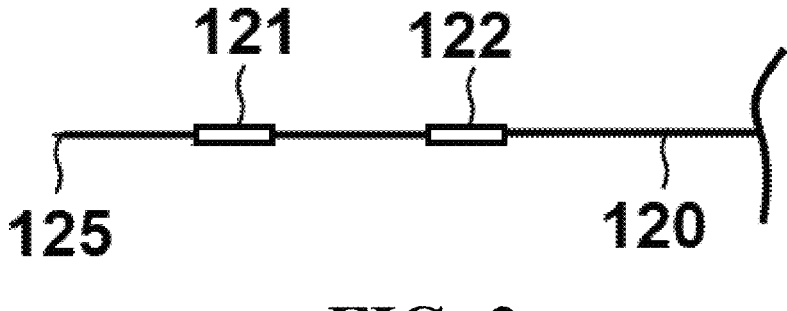
FIG. 3 illustrates a schematic view of a pulse generator and wireless communication device of the embodiment of FIG. 1.

Referring initially to FIGS. 1-3, an apparatus 100 comprises an implantable pulse generator 110 and a microelectrode catheter 120 comprising a distal end 125 with one or more electrodes 121 and 122 (shown in FIG. 2) implanted in a cranial subarachnoid space of a subject 150. In the illustrated embodiment implantable pulse generator 110 can send and/or receive wireless signals 131 to and from a wireless communication device 130. It is understood that the images shown in the figures are exemplary in nature and that other embodiments may comprise features or elements that differ from those shown. For example, the location of the implantable pulse generator 110 shown in FIG. 1 may be different in other embodiments, including for example, in locations along the spinal subarachnoid space 152 that are farther away from the brain than the location shown in FIG. 1. FIG. 3 illustrates exemplary embodiments of implantable pulse generator 110 and wireless communication device 130 transmitting wireless signals 131 according to exemplary embodiments of the present disclosure.

In particular embodiments, apparatus 100 is configured as a wireless system implanted via a minimally invasive, percutaneous surgical approach that takes advantage of the subarachnoid space to guide catheter electrodes to electrically interface with the central nervous system. In this endocisternal context, the cisternal space is defined as the reservoirs filled with CSF and encompasses both subarachnoid and ventricular spaces of the spinal cord and brain. This approach enables an extremely flexible deployment of the system to a multitude of targets through a simple lumbar puncture.

Figure 4:
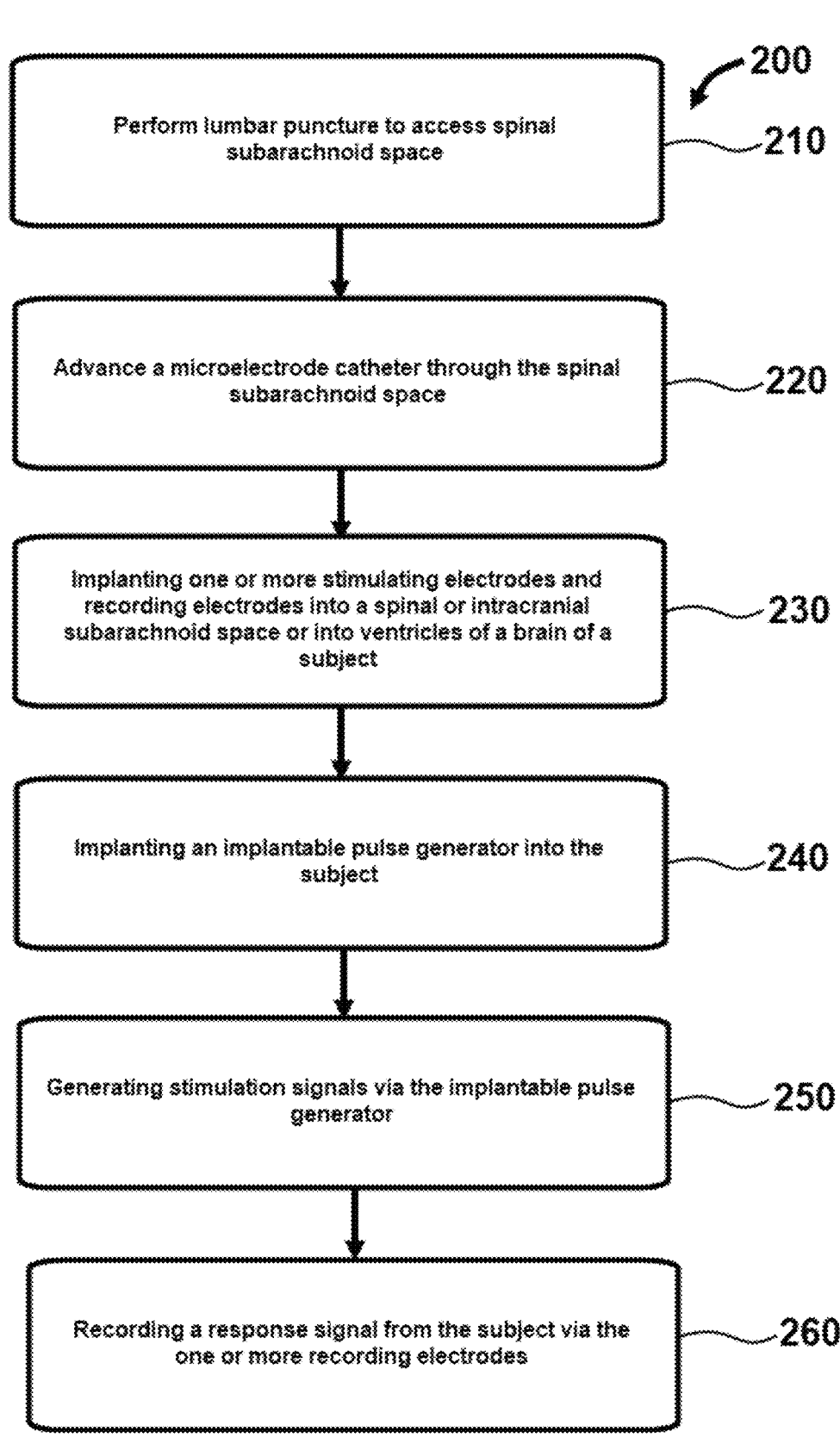
FIG. 4 illustrates steps of a method according to an exemplary embodiment of the present disclosure, including the embodiment of FIG. 1.

Steps of an exemplary embodiment of a method of use for apparatus 100 are shown in FIG. 4. In this embodiment method 200 comprises a step 210 of performing a lumbar puncture to access spinal subarachnoid space. Method 200 also comprises a step 220 of advancing a microelectrode catheter through the spinal subarachnoid space and a step 230 of implanting one or more stimulating electrodes and recording electrodes into a spinal or intracranial subarachnoid space or into ventricles of a brain of a subject. In addition, method 200 comprises a step 240 of Implanting an implantable pulse generator into the subject and a step 250 of generating stimulation signals via the implantable pulse generator. Furthermore, method 200 comprises a step 260 of recording a response signal from the subject via the one or more recording electrodes.

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Figure 6:
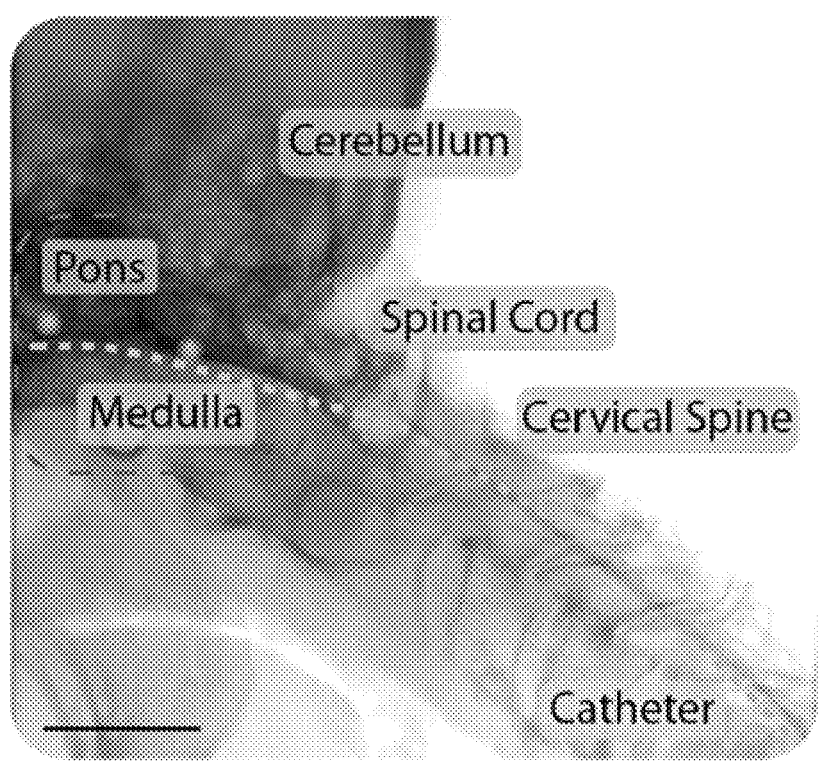
FIG. 6 illustrates images of a third ventricular cisternogram showing the path and guidance of a catheter according to an exemplary embodiment of the present disclosure, including the embodiment of FIG. 1.
Figure 6:
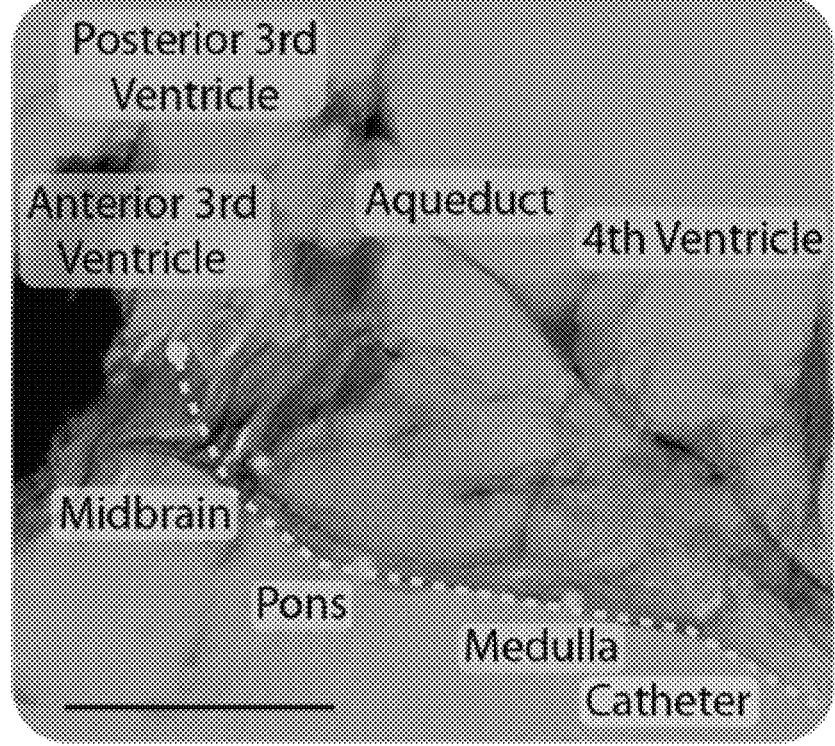
Figure 12:
FIG. 12 illustrates an image of a catheter electrode according to an exemplary embodiment of the present disclosure going through the craniocervical junction and navigating to frontal cortex of a subject brain.

To demonstrate viability of exemplary embodiments of the present disclosure, navigation of the spinal and cranial subarachnoid space in human cervical cadaver models was performed in testing. Entering a catheter through the cervical spinal subarachnoid space provided the ability to guide a microcatheter (0.6 mm distal tip) into the frontal convexity as well as into the third ventricle in a human cadaver under image guidance using cisternography as shown in FIG. 6. As can be seen on a cisternogram, the catheter path, highlighted in yellow, passes anterior to deep brain structures like the medulla and pons prior to reaching the third ventricle by traversing its floor. Preliminary studies of reversed third ventriculostomies showed potential safety of the procedure with no observable damage in histology of the third ventricle, mid brain, and pons. Additionally, to guide the development of endocisternal neural interfaces, the inventors characterized the critical dimensions for which an implant could fit within this space. From a lumbar puncture in the lower back, the width of the subarachnoid space falls within the millimeter regime, indicating that mm to sub-mm interfaces could be moved throughout this space [31,32]. Measured across 10 patients, the smallest dimension was found in the cervical spinal region with a measured dimension of 2.95+/−0.81 mm. The subarachnoid space remains fairly constant through the lumbar, thoracic, and cervical spinal areas before opening up in the craniocervical junction and narrowing again into the subarachnoid spaces of the brain as documented in FIG. 7. 3D reconstructions of the CSF space showed the mm-sized navigable volumes along with a representative path of the catheter to reach the frontal cortex of the brain (as shown in FIG. 12). In addition to the human cadaver studies, the inventors validated the ECI in a clinically relevant large animal model. Ovine models have been shown to be an excellent representation for human spinal research [33,34]. Thus, the inventors tested our neural stimulation and recording system in the central nervous system of sheep models interfacing the wireless implantable pulse generator, MagnetoElectric BioImplanT (ME-BIT), with the catheter electrode (FIG. 8) (n=12, 10 acute and 2 survival studies).

Figure 13:
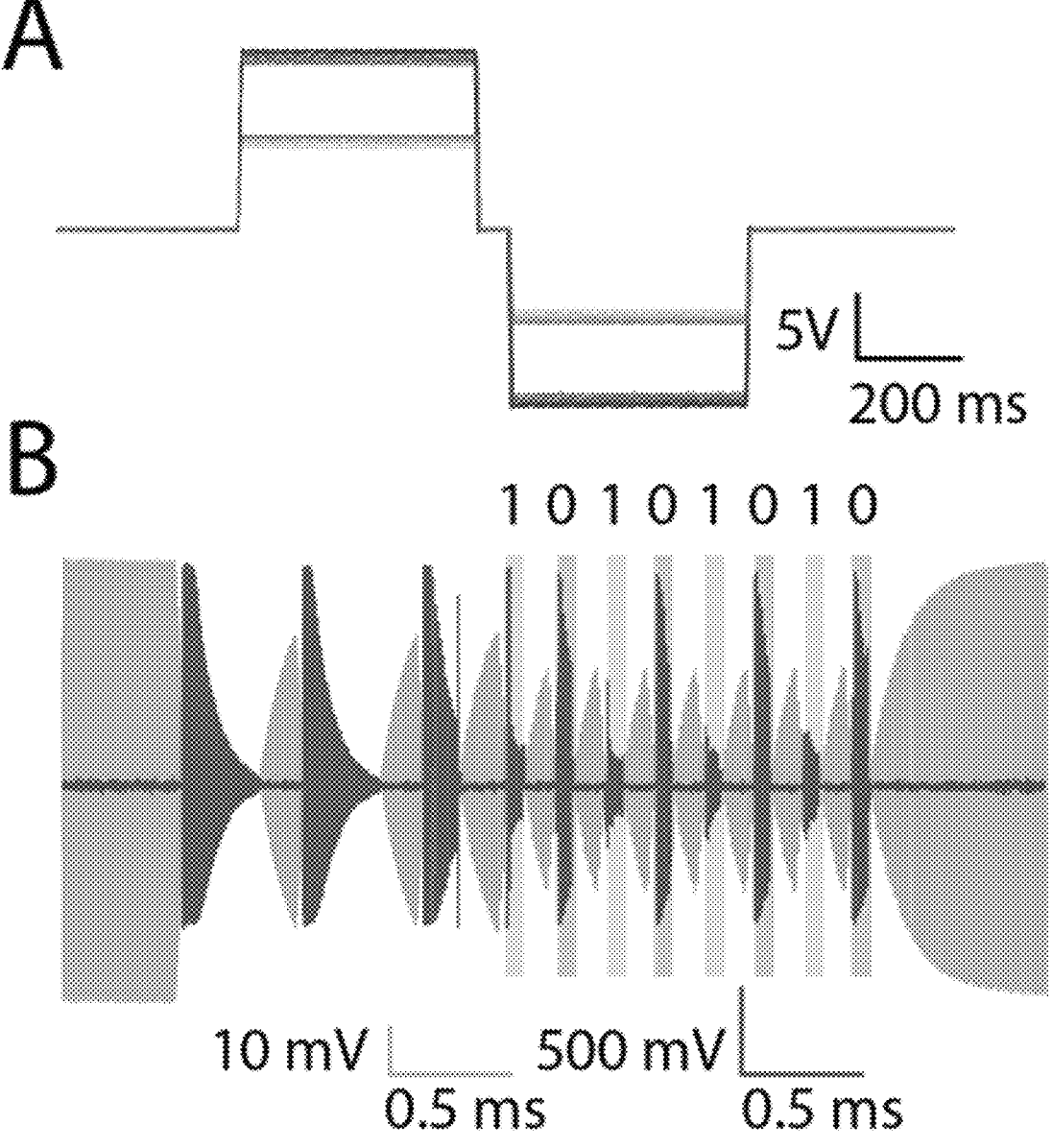
FIG. 13 illustrates a graph of programmable voltage-controlled stimulation pulses generated by the magnetoelectric wireless implant according to an exemplary embodiment of the present disclosure.

Using a millimeter-sized battery-free implantable stimulator the inventors demonstrated multi-site electrical stimulation and recording through the ECI. Magnetoelectric materials, which are thin films that convert magnetic fields to electric fields, were utilized to engineer miniaturized battery-free bioelectronics to serve as the implantable pulse generator [35]. Using a magnetic field allows exemplary embodiments to send power and data into the implant to have programmable stimulus pulses with varying amplitudes up to 14.5 V, pulse widths, and duty cycles. In addition, the magnetic field also provides the ability to take advantage of recently developed magnetoelectric backscatter to also wirelessly record physiologically relevant signals through this endocisternal neural interface (FIG. 9, FIG. 13).

Briefly, exemplary embodiments of the implant comprise a printed circuit board coupled with a magnetoelectric films and a bias magnet to optimize the power transfer on the films. In certain embodiments, these components are assembled inside a glass capsule and sealed with medical grade epoxy with stimulation and recording leads coming out of the package (FIG. 3). The resulting size and weight of the implant is around 9 mm×9 mm×11 mm and 1.1 g. The ME-BIT is placed in a small pocket in the back of the animal and electrically wired to the catheter electrode that is inserted into the subarachnoid space. Additionally, the system includes the wireless transmitter that uses a litz wire pancake coil coupled with recording coils on a PCB (FIG. 3) capable of powering at centimeter depths [37].

Due to the flexibility of deployment, the inventors navigated the catheter electrodes starting at the lower back up the spinal canal and into the brain. The inventors were able to stimulate throughout the spinal cord from lumbar up to cervical regions. Powering the electrode with the ME-BIT and applying a 14.5V, 250 μs pulse width monophasic pulse train of 10 pulses with 2.75 ms interpulse width at 0.8 Hz activated the spinal cord. The inventors observed muscle contractions and measured compound muscle action potentials (CMAPs, FIG. 7, FIG. 14) with EMG needles on the back of the sheep. The catheter was further navigated through the craniocervical junction to enter the brain.

Figure 9:
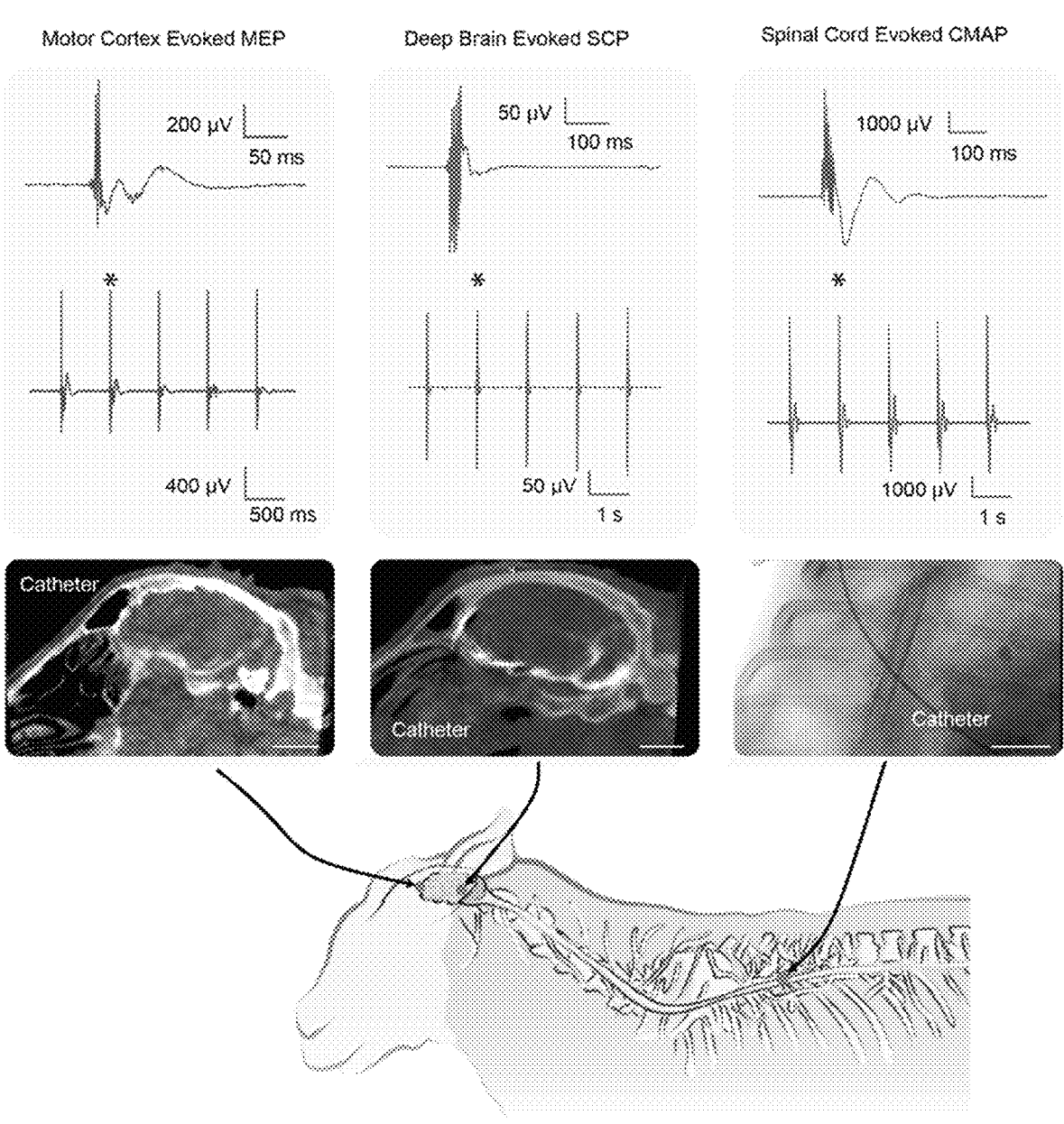
FIG. 9 illustrates recordings of wireless neural stimulation through an endocisternal interface of an exemplary embodiment of the present disclosure.
Figure 14:
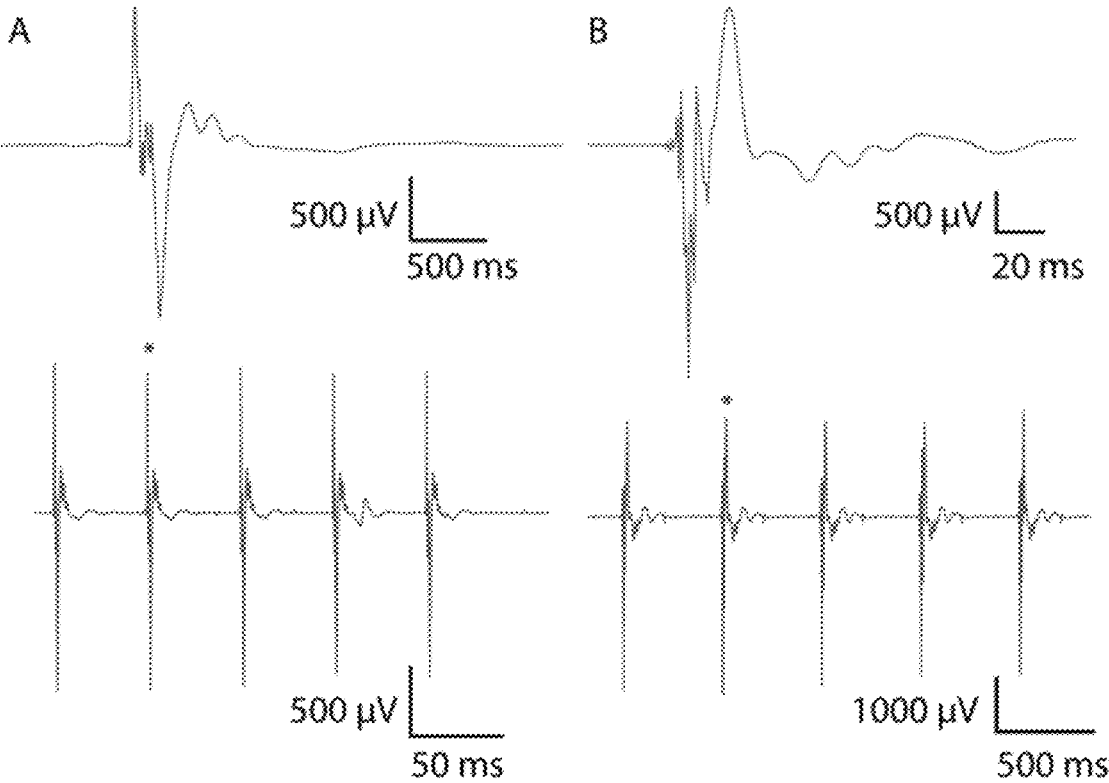
FIG. 14 illustrates stimulation data recorded according to an exemplary embodiment of the present disclosure.
Figure 15:
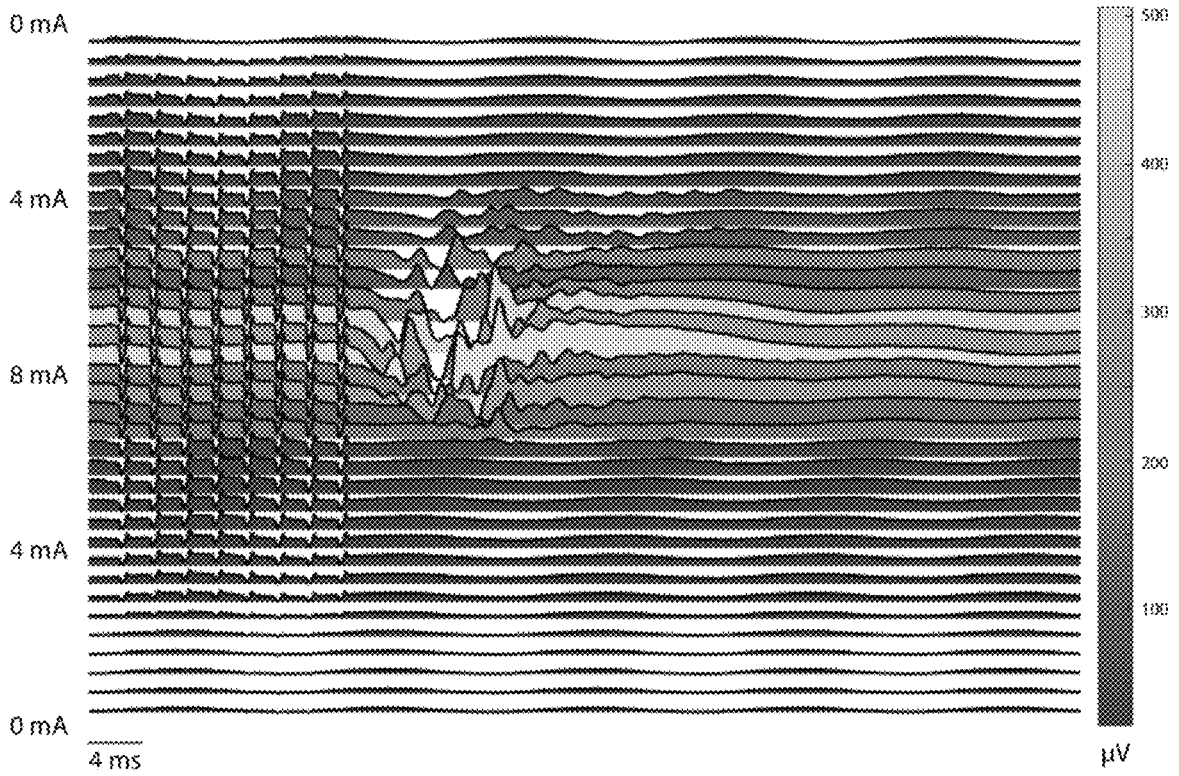
FIG. 15 illustrates a waterfall plot showing voltages recorded at different stimulation currents according to an exemplary embodiment of the present disclosure.

Without any burr holes or craniotomies, the inventors were able to apply the same electrical stimulation waveform of 14.5V (250 μs pulse width, 2.75 ms interpulse width, 10 pulses) at 2 Hz to stimulate the motor cortex where muscle contractions were observed in the hind leg of the sheep and measured corresponding MEPs (FIG. 9, FIG. 14). Additionally, deep brain structures (thalamus through ventricular surface) were stimulated at 0.8 Hz and recorded downstream activation of the central nervous system with spinal cord potentials. In fact, by increasing the number of stimulation pulses, the inventors confirmed that they indeed elicited a central response through observations in latency shifts as they increased stimulation amplitude (FIG. 15).

Figure 10:
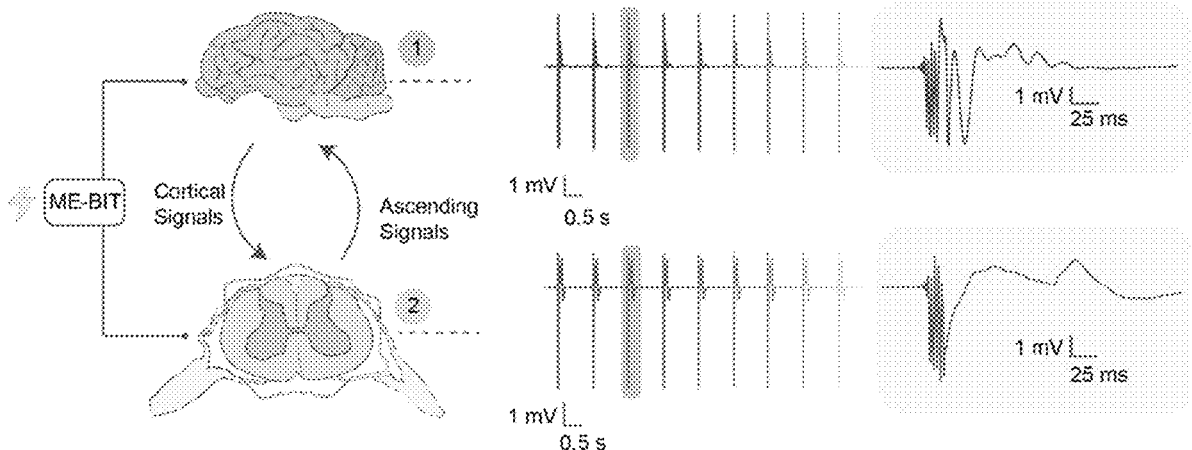
FIG. 10 illustrates a schematic showing the synchronized stimulation of brain and spinal cord with the magnetoelectric powered implant of an embodiment according to the present disclosure.
Figure 22:
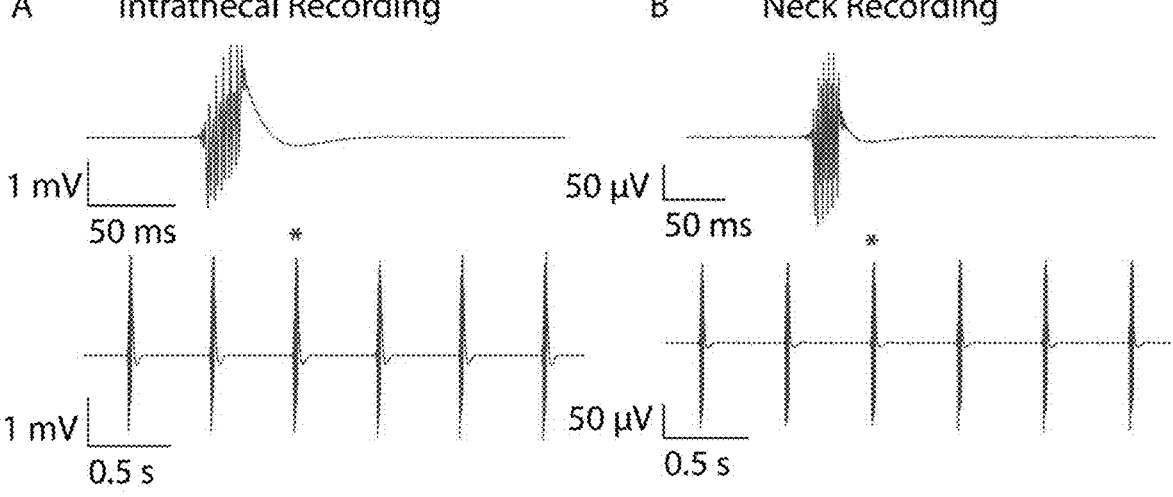
FIG. 22 illustrates recording from intrathecal space with stimulation according to an exemplary embodiment of the present disclosure.

Furthermore, the inventors simultaneously fit two catheter electrodes with diameters 0.6 mm within the subarachnoid space with the first electrode navigated to the cortex of the brain and the second catheter electrode on the spinal cord in the thoracic region (FIG. 6). The inventors were able to apply simultaneous electrical stimulation using one ME implantable pulse generator to synchronously stimulate both brain and spinal cord demonstrating simultaneously access. Simultaneous multisite access remains highly relevant for developing neural interfaces that can perform closed loop and coordinated stimulation and recording across different neural structures 39,40. Recording the local field potentials at the site of stimulation in both the head and leg yielded measurable MEPs and CMAPs where the stimulus artifacts are both time locked (FIG. 10). Certain embodiments of the present disclosure may comprise catheter electrodes that enable multichannel functionality with exposed electrodes along the length of the catheter to reduce the number of catheters implanted in the body. The inventors verified the recorded electrophysiologic signals were not artifacts by stimulating the sheep post-euthanasia and recorded in the intrathecal space and in the neck muscles (FIG. 22). The inventors did not observe any muscle response and could only detect the stimulation artifacts.

Figure 11:
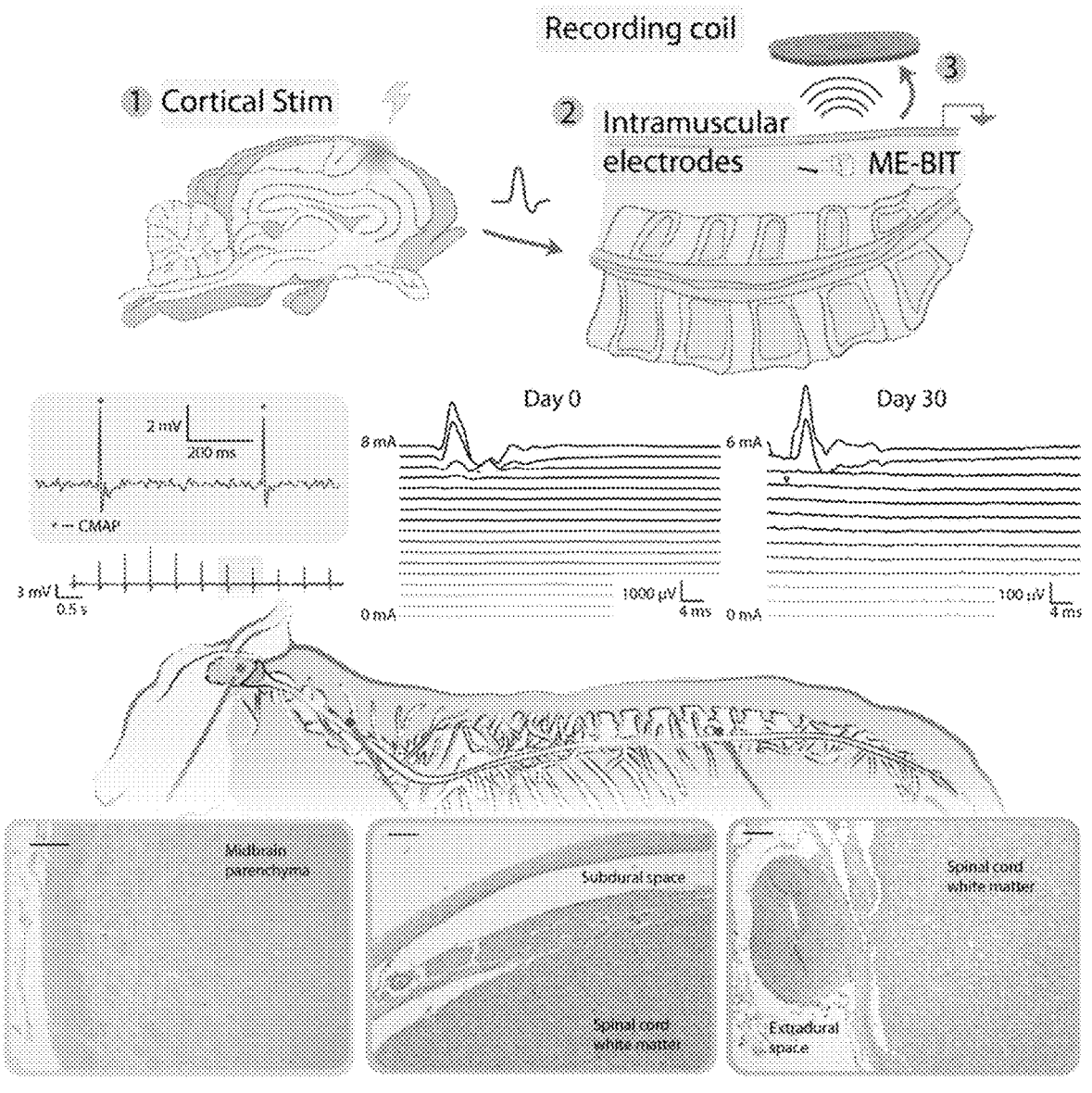
FIG. 11 illustrates a schematic of a data collection setup to validate wireless recording data of an embodiment according to the present disclosure.
Figure 16:
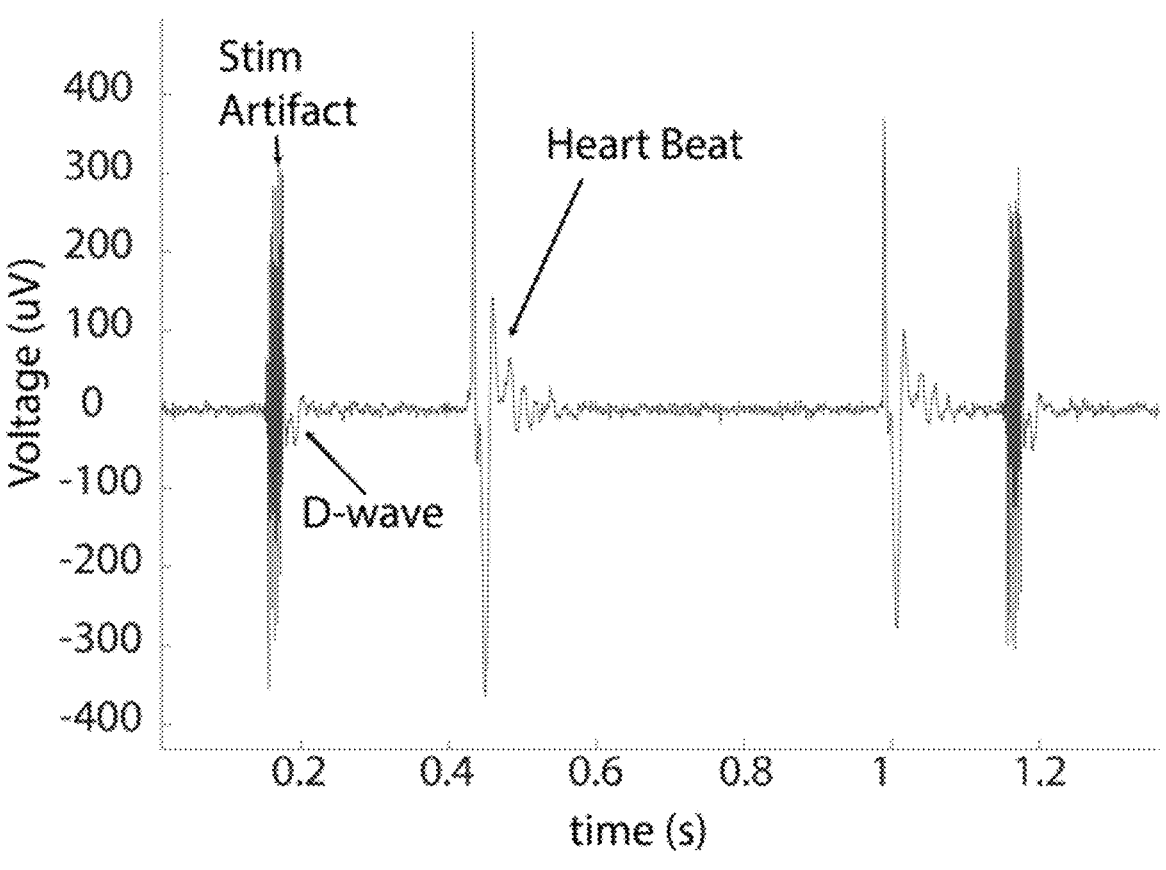
FIG. 16 illustrates a catheter recording from within the subarachnoid space according to an exemplary embodiment of the present disclosure.
Figure 17:
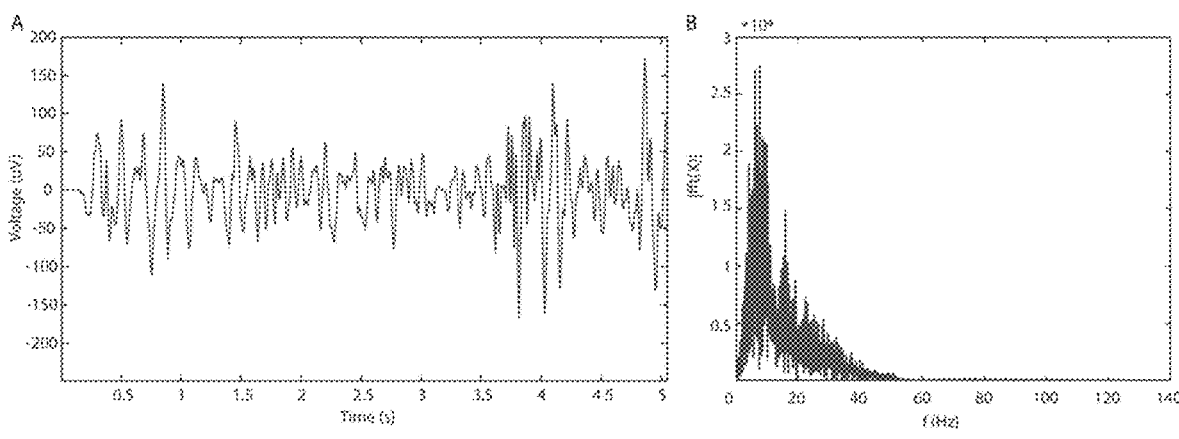
FIG. 17 illustrates an EEG recording through catheter electrode space according to an exemplary embodiment of the present disclosure.

The inventors further tested the functionality of this endocisternal neural interface to wirelessly record electrophysiologic signals. The inventors implemented a wireless backscatter protocol with 3 bits for downlink and 8 bits for uplink where the magnetic field is pulsed, and the magnetoelectric ringdown characteristics are measured while the field is off. The data '0' and data '1' are encoded by changing the applied electric load to the magnetoelectric films (FIG. 14) [35]. The inventors implanted a catheter electrode in the brain over the motor cortex connected to an ME stimulator, and intramuscular recording electrodes were connected to a second recording ME implant. The inventors then electrically stimulated the motor cortex with 1 Hz pulses through the catheter electrode and hypothesized that they could wirelessly record the downstream muscle activity (FIG. 11). Indeed, the inventors observed CMAPs associated with muscle contractions (FIG. 11). Due to current limitations in the sampling frequency of magnetoelectric backscatter and gain of the wireless recording circuit, the inventors also used a benchtop recording system to record smaller magnitude signals such as spinal cord nerve potentials where D-wave activity upon brain stimulation was observed (FIG. 16). Additionally, using the benchtop system, EEG from the frontal convexity of the brain could be recorded. (FIG. 17).

Figure 18:
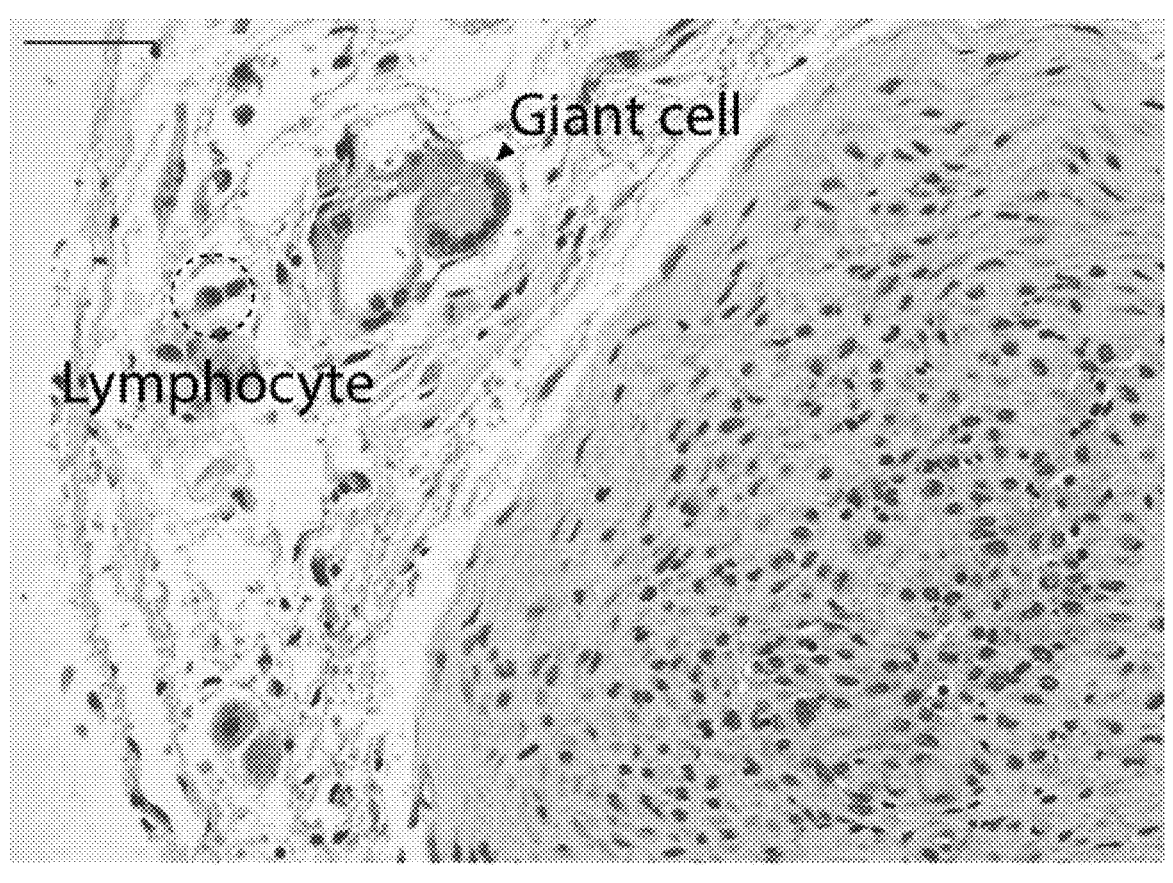
FIG. 18 illustrates a high-power image of lumbar epidural reactive vasculature from a sheep implanted according to an exemplary embodiment of the present disclosure.
Figure 19:
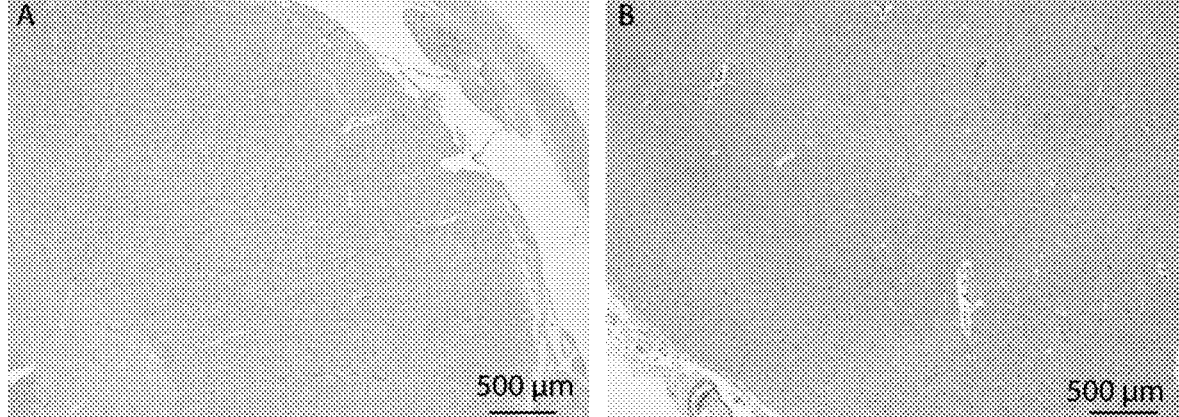
FIG. 19 illustrates a cervical spinal cord histology in a survival sheep implanted according to an exemplary embodiment of the present disclosure.

When implanting for more than 30 days in the sheep model stable stimulation thresholds were found on day 0 and day 30 suggesting good chronic performance of the endocisternal neural interface (n=2). With the catheter electrode placed in the frontal convexity, by increasing the amplitude of a single stimulation pulse with a 250 μs pulse width, muscle contraction was observed to begin at around a stimulus current of 6.5 mA (FIG. 11). At day 30, a similar stimulation threshold of around 5.5 Ma was observed, which indicates no noticeable changes in the electrical connectivity of the interface to the tissue. The catheter also remained stable in position. Differences in the amplitude of the recorded muscle activity are likely due to variation in placement of EMG recording needles. In addition to surviving the animal for 30 days with no neurological deficits observed, explantabilty of the ECI was also demonstrated, and the sheep survived for an additional week, again with no neurological deficits. This unique property of the endocisternal interface will allow this to be used in transient bioelectronic therapies where explantability is required [41]. A week after explantation, the sheep was sacrificed and upon conducting histology, no subdural, subarachnoid, or parenchymal inflammation or damage at any level in the spinal cord, midbrain, cerebrum, or cerebellum was found (FIG. 11). There was only some mild extradural inflammation found in the lumbar region which could be a result of the lumbar puncture (FIG. 18). Otherwise, spinal cord, brainstem, cerebrum, and cerebellum were all normal after the 30-day chronic implantation and explantation. In another sheep that was survived for a month, no inflammation was found in the brain or spinal cord with only minor cervical inflammation in the subdural space and minimal inflammation in the leptomeninges of the midbrain which is within expectations for any implant. (FIG. 19).

The preliminary feasibility and safety of endocisternal navigation and minimally invasive stimulation and recording from ECI implants shown here in acute and survival animal studies suggests the potential of future minimally invasive ECI implants and transient therapies where the ECI implant can be safely removed after several weeks [41].

While an initial catheter embodiment is shown and described herein, other embodiments may incorporate different catheter interface and other geometries, including for example, mesh electrode arrays that would enable multiplexed stimulation through the subarachnoid and ventricular spaces. Illustrated embodiments have two electrode channels which enable bipolar stimulation in one channel or monopolar stimulation with two channels and a reference electrode on the implantable pulse generator. Other embodiments may comprise multi-channel arrays similar to strip electrodes used in spinal cord stimulators [42]. While embodiments discussed herein were explanted after more than one month in a large animal, other embodiments may include longer chronic implantation and explantation of different electrode interfaces. One advantage of these endocisternal neural interfaces is the ability to access both spinal cord and brain structures simultaneously, which is also important for other applications such as paralysis rehabilitative therapies where coordinated stimulation and recording between brain and spinal cord can induce plasticity and recovery [39,40].

The ability of these endocisternal neural interfaces to reach the entire brain convexity along with deep brain structures through the ventricles enables neuromodulation of difficult to reach areas through a simple lumbar puncture. Other known access to the subarachnoid space such as C1/2 and suboccipital punctures may be possible in additional embodiments according to the present disclosure. Suboccipital puncture can potentially access the dentate nucleus to enhance stroke rehabilitation through deep brain stimulation [43]. As demonstrated in this disclosure, exemplary embodiments were able to not only access the motor cortex which has implications for brain machine interfaces to restore motor functions, but also deep brain structures like the thalamus through the third ventricle which can be used to treat movement disorders [44]. Additionally, exemplary embodiments of the present disclosure allow for easier access to certain brain areas such as the orbitofrontal region (potential target for refractory psychiatric disorders) where traditional surgical access is difficult [45,46].

Figure 21:
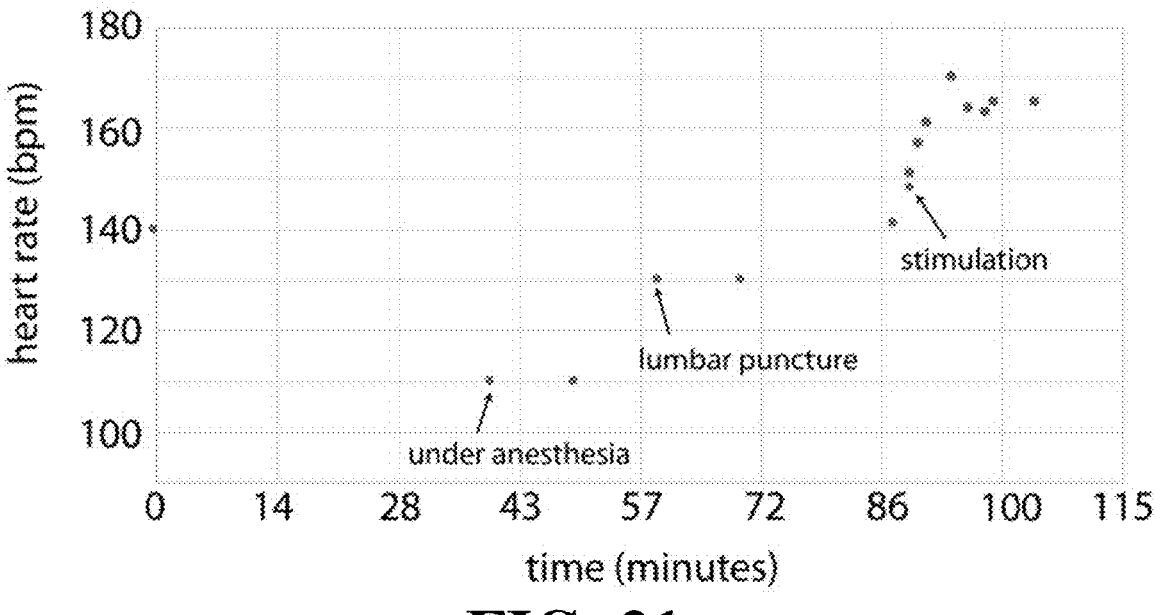
FIG. 21 illustrates heart rate measurements from a sheep during procedures according to an exemplary embodiment of the present disclosure.

Additional embodiments according to the present disclosure may utilize navigation under multi-modality image guidance (e.g. the merge of MRI and myelogram), and further testing may provide more targeted and focal stimulation. This testing can inform the optimal stimulation parameters that produce a desired neuromodulatory effect while minimizing side effects like pain or sensation (FIG. 21). Moreover, exemplary embodiments of the present disclosure should be MRI safe as previous studies of wireless implants with 50 times more magnetic material demonstrated safety with minimal heating. Imaging artifacts may need to be considered for specific applications [47]. Additionally, exemplary embodiments of the ECI can be made with non-magnetic material that is MRI-compatible. An access system specifically designed for endocisternal navigation may also be utilized to optimize access and navigation in the endocisternal space. The minimally invasive surgical approach discussed herein may help increase the adoption rates for these implants as they become more minimally invasive. Especially as more neurotechnology is primed for translation, it becomes more important to minimize the risk and recovery for patients to increase adoption. With interfaces like those discussed herein, that can access brain and spinal cord with a catheter, one can envision neural interfaces becoming as ubiquitous as other bioelectronic implants such as cardiac pacemakers or cochlear implants.

In one embodiment according to the present disclosure, under direct visualization, a 4 F Terumo slender sheath was directly inserted into the dorsal cervical spinal subarachnoid space of the cadaver. 20 cc of iodinated contrast was infused through the sheath to provide a cisternogram and myelogram for navigation. Through the sheath, a Synchro 0.014" microwire (Stryker, Kalamazoo, Michigan) is used to navigate a SL10 microcatheter (Stryker, Kalamazoo, Michigan) from the cervical subarachnoid space to the intracranial subarachnoid space by staying ventral to the spinal cord and midline under fluoroscopic guidance (Artis Zeego, Siemens). Once intracranially and as described previously, the catheter was navigated into the third ventricle through traversing the floor of the third ventricle behind the clivus (FIG. 9) [48]. Third and fourth ventriculograms were performed through the microcatheter. While human cervical cadaver models were used for these preliminary navigation studies with cervical access, future ECI's will likely be implanted through puncture at the low lumbar level below the end of the spinal cord to improve safety of the access.

As shown in FIG. 3 an exemplary embodiment of the implantable pulse generator 110 comprises a custom printed circuit board (PCB) 111, two 7.5×3 mm magnetoelectric films 112 (resonant frequency 218 kHz), and a glass enclosure 113. It is understood that other embodiments of the implantable pulse generator may comprise different components or a different arrangement of the components. In certain embodiments, the leads are connected to the glass device using a conductive epoxy attachment to sputtered electrodes. The device can be programmed to output a train of 10 voltage-controlled, programmable amplitude, biphasic pulses, up to a rate of 500 Hz when triggered by the external transmitter. With a greater than 50 mW power supply, the implant can potentially be designed to reach higher stimulation frequencies (>2 kHz) for other applications [49]. In certain embodiments the external transmitter communicates with the device using pulse-width modulated downlink communication and additional details can also be found in Woods et al.

In the embodiment discussed herein, a driver system was built high-electron-mobility gallium-nitride transistors (GS61008T, GaN Systems) as the H-bridge stage with an optimized magnetic board layout for high frequency and power switching operations [50]. This magnetic field driver was controlled using a custom script through Waveforms where control signals were sent through an Analog Discovery Pro (ADP3450/ADP3250). Together this system drives current through a resonant coil that is wrapped using 18 AWG litz wire (MWS Wire) and resonated with high voltage rated capacitors (WIMA).

During testing of embodiments disclosed herein, sheep were stimulated with the ECI on day 0 and survived for 30 days. After the month, the interface was explanted after re-stimulation and the sheep are survived for another week before being sacrificed. Tissue slices were taken of both the spinal cord and the brain. Standard Hematoxylin and Eosin (H&E) staining was used to visualize the tissue anatomy.

Figure 20:
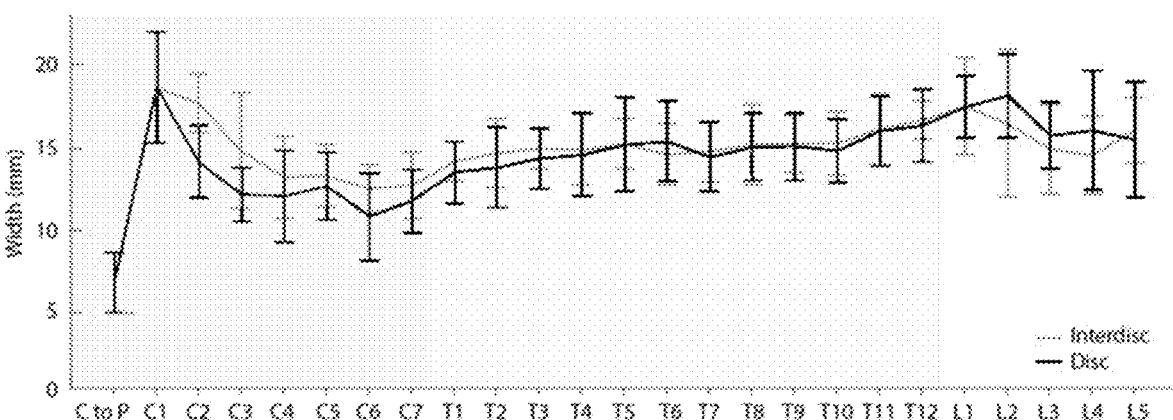
FIG. 20 illustrates measurements of spinal canal width taken from the MRIs of human patients suitable for implantation according to an exemplary embodiment of the present disclosure.
Figure 20:
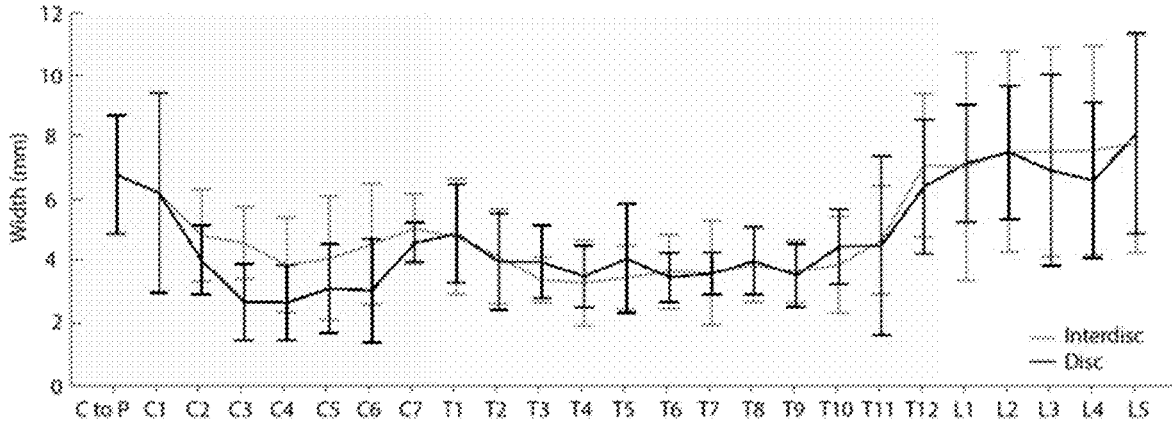
Figure 20:
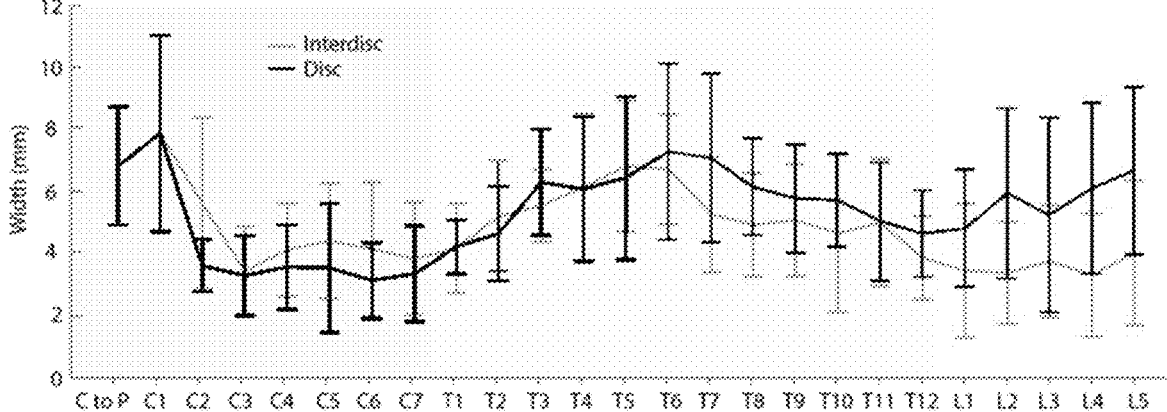
Figure 23:
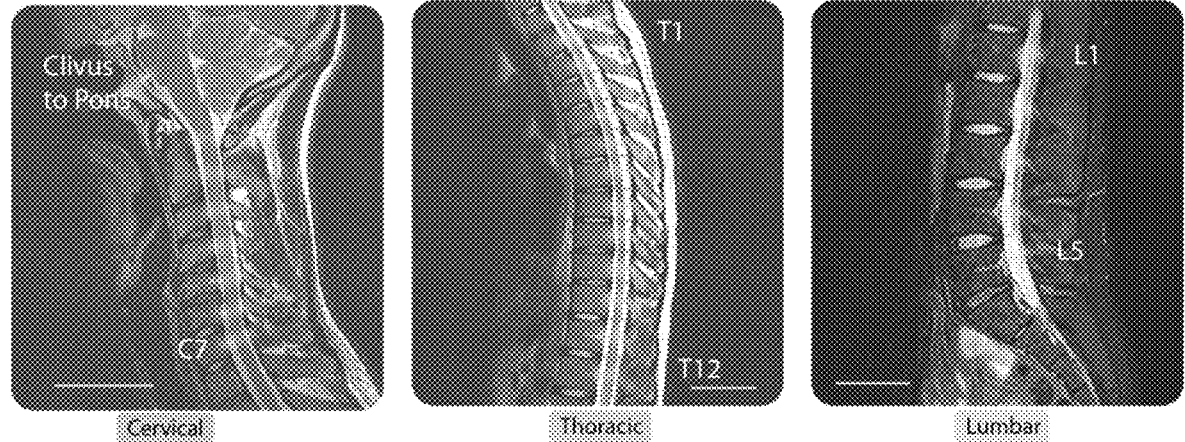
FIG. 23 illustrates images showing spinal canal measurements.

Results of sagittal T2 weighted fast relaxation fast spin echo sequence (FRFSE) MRI images of the cervical, thoracic, and lumbar spinal canal in 10 live human patients, conducted without the administration of intravenous (IV) contrast (1.5 T GE and Siemens and 3 T Siemens). Average age of the included patients was 36.1 years old (median: 33 y/o, range: 15-78 y/o). 6 of the patients were male and 4 were female. The average body mass index (BMI) was 27.8 kg/m2 (median: 25.54 kg/m2, range: 18.01-45.63 kg/m2). Measurement of the spinal canal was performed using Picture Archiving and Communication System (PACS) built in measurement tools. Dimension of the entire spinal canal was measured at the center of the vertebral body and at the vertebral disc (labeled disc and interdisc) along with dimensions both anterior and posterior to the spinal cord (FIG. 23, yellow lines show interdisc measurement while orange lines denote vertebral disc measurement). The final average between posterior and anterior measurements are reported in the main figure (FIG. 20 top graph light gray lines).

The animal procedures were conducted in accordance with regulations of the IACUC (Protocol no. 2110061). Twelves female Western Range sheep, weighing approximately 40-50 kg, received a 7-day acclimation period prior to any procedure. For both acute and chronic sheep experiments, general anesthesia was induced by ketamine (5 mg kg-1) and xylazine (0.2 mg kg-1) intramuscularly, followed by intubation by veterinary personnel. Mechanical ventilation was maintained under a mixture of oxygen and isoflurane (1-3%). Routine physiological monitoring was performed. Animal was placed in prone position to allow palpation of anatomical landmarks and initiation of the lumbar puncture.

Under fluoroscopic guidance (CIOS Spin 3D, Siemens Healthineers), the lumbar subarachnoid space of the sheep was accessed with an 18 G spinal needle. Once access is confirmed with spontaneous flow of cerebrospinal fluid (CSF), an 0.018" wire is threaded under fluoroscopic guidance up to the thoracic subarachnoid space. Using the Seldinger technique, the spinal needle is then exchanged for a 5 F Glidesheath Slender introducer sheath (Terumo, Somerset, New Jersey). A myelogram is then performed through the sheath to ensure proper placement (e.g. not in the epidural space). A Synchro 0.014" microwire (Stryker, Kalamazoo, Michigan) is used to navigate an Echleon 10 microcatheter (Medtronic, Minneapolis, Minnesota) from the lumbar subarachnoid space to the intracranial subarachnoid space by staying ventral to the spinal cord and midline under fluoroscopic guidance. Once intracranially, the catheter can be navigated along the clivus to the orbitofrontal cortex and around the frontal pole to the frontal convexity (target of stimulation FIG. 6). Alternatively, it can access the third ventricle through the floor of the third ventricle. Through the third ventricle, the thalamus can be accessed (FIG. 6). Electrophysiologic recordings were done on a Cadwell IOMax using subdermal needles for the EMG recordings, otherwise the benchtop recording system was connected to the endocisternal catheter electrodes. Additionally, the benchtop system was used for thresholding experiments. Wireless recording was done using the magnetoelectric implant.

Two sheep were used for survival chronic implantation experiments and the other 10 sheep were used for acute stimulation and recording experiments. Successful stimulation and recording were done in all 12 of the sheep. The inventors stimulated in the motor cortex of a subject sheep and observed the resulting MEPs in the sheep's back. The heart rate was also recorded for one of the sheep (FIG. 21). The sheep was induced when brought into the surgical suite. Once stabilized, its heart rate was monitored under anesthesia. After lumbar puncture and increasing stimulation from 0 to 8 mA (250 ms pulse widths) of the motor cortex, the increase in heart rate was noticed following extended stimulation, which indicates a potential pain response, likely from the stimulation of the dura. In existing neuromodulatory devices, optimizing the duty cycle, duration, and waveform has been effective in limiting off-target activation of tissue [51]. It is expected that similar work will be needed for ECIs depending on the therapeutic target (e.g. cortical targets).

To validate the recorded physiologic signals, the inventors recorded in the intrathecal space and on the neck muscles of one sheep post-euthanasia. After 10 minutes, the inventors stimulated the catheter electrode placed in the motor cortex region with the ME-BIT (2 Hz, 14.5V, 250 μs pulse width, 10 pulses, 2.75 ms interpulse width) and recorded through a catheter electrode in the intrathecal space (lumbar region) and intramuscular electrodes in the neck with the Cadwell IOMax.

Figure 5:
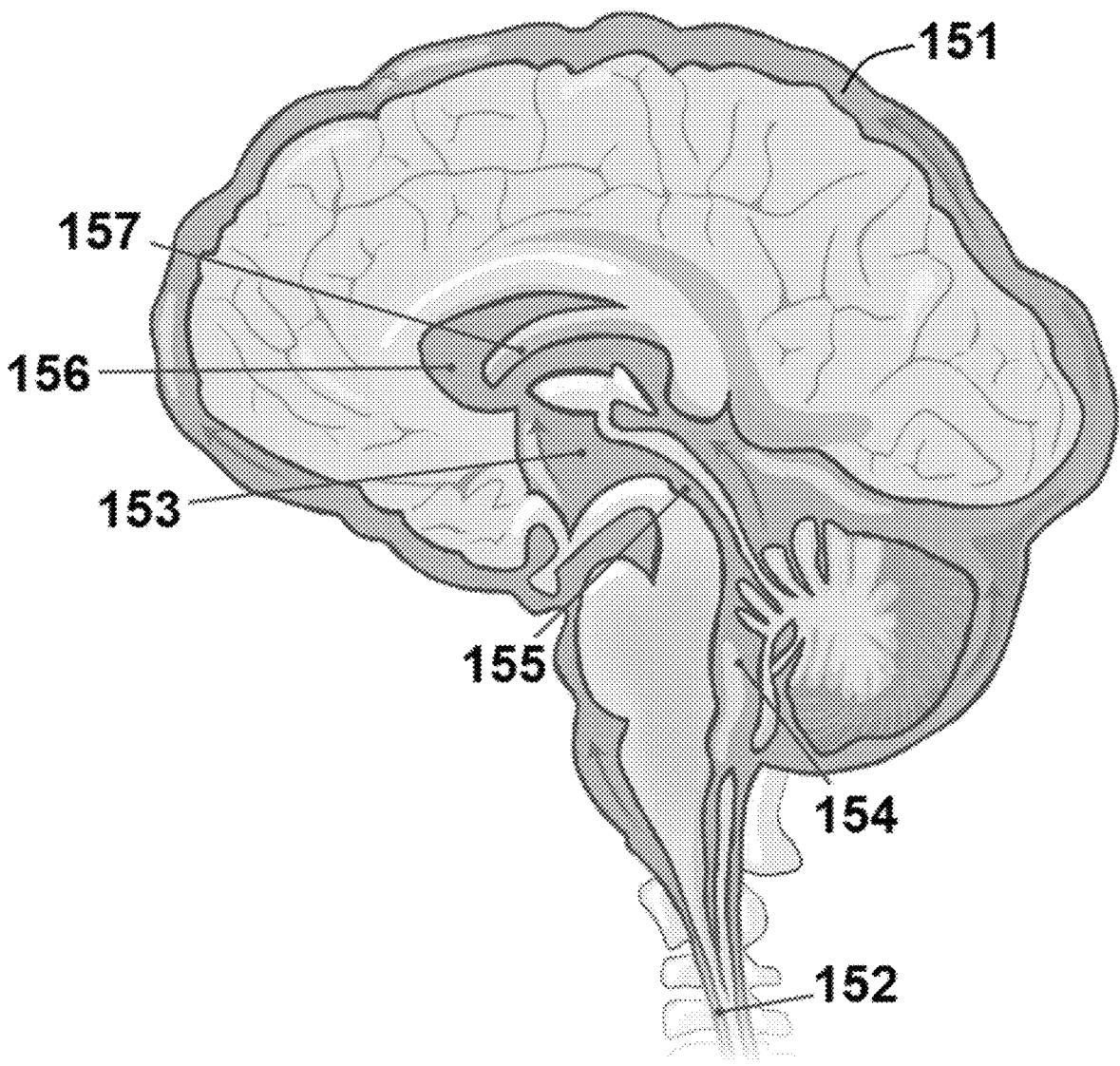
FIG. 5 illustrates a cross section of cranial subarachnoid space and spinal subarachnoid space with specific locations for implanting electrodes of the embodiment of FIG. 1.
Figure 7:
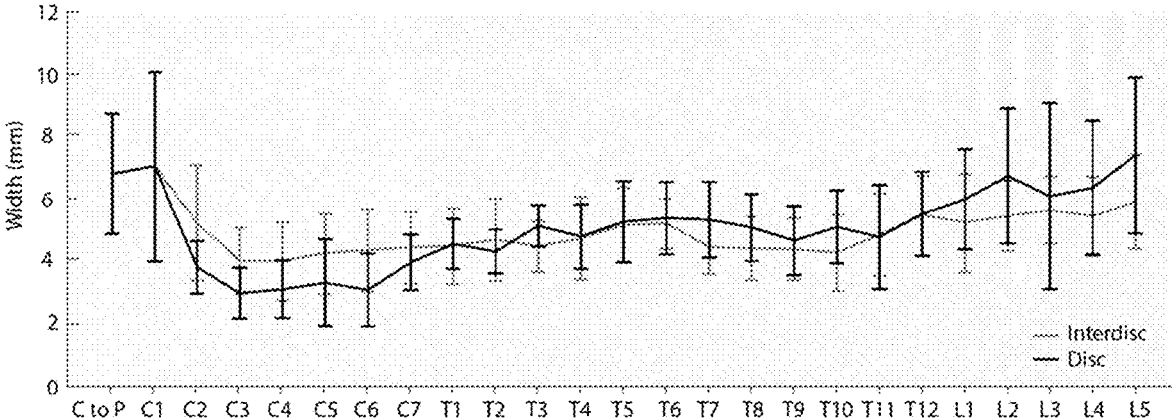
FIG. 7 illustrates a graph of the width of the subarachnoid space for subjects suitable for implantation of an exemplary embodiment of the present disclosure, including the embodiment of FIG. 1

FIG. 5 illustrates a cross section of cranial subarachnoid space 151 and spinal subarachnoid space 152 with specific locations in subarachnoid space 151 identified, including potential locations for implanting stimulating and/or recording electrodes. In particular, FIG. 5 illustrates a third ventricle 153, a fourth ventricle 154, a cerebral aqueduct 155, a lateral ventricle 156 and choroid plexus 157 in the section view shown. FIG. 6 shows images of a third ventricular cisternogram in human cadaver models showing the path and guidance of a catheter into the third ventricle along with major anatomical features. The lower image is a zoomed image of the top image (scale bars: top=50 mm, bottom=25 mm). FIG. 7 illustrates a graph of the width of the subarachnoid space in the spinal canal towards brainstem measured across 10 patients with MRI. The measurements are an average of the anterior and posterior subarachnoid spaces with error bars demonstrating standard deviation, where the black line is measured at vertebral disc level and the gray line is measured at intervertebral disc level.

Figure 8:
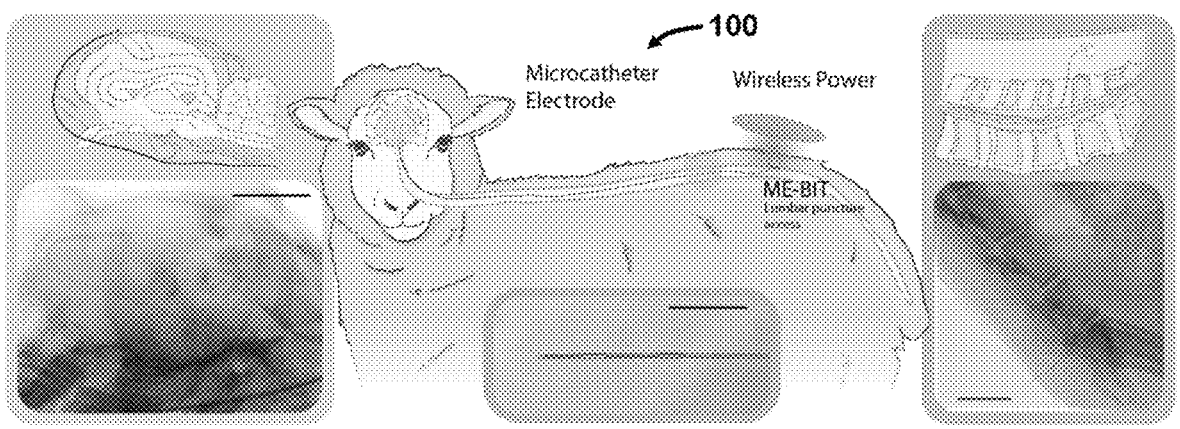
FIG. 8 illustrates a schematic of an embodiment according to the present disclosure deployed in a sheep model.

FIG. 8 illustrates a schematic of apparatus 100, sometimes referred to herein as an endocisternal interface (ECI), deployed in a sheep model with implanted magnetoelectric pulse generator (ME-BIT) and wireless power transmitter. The left schematic shows a catheter navigated to the frontal cortex of the sheep brain and corresponding X-ray below with the catheter visible (scale=50 mm). The center image shows a magnified image of the two-channel catheter electrode (scale=4.5 mm). The right schematic shows the pulse generator implanted in the lumbar region of the sheep with the catheter electrode entering subarachnoid space along with a corresponding X-ray of a lumbar puncture with a catheter (scale=50 mm).

Referring now to FIG. 9, recordings of wireless neural stimulation through an endocisternal interface in sheep are shown. The panel on the left shows recordings of motor evoked potentials recorded from the hind leg of the sheep from stimulation in the motor cortex. A corresponding CT scan shows the catheter tip circled in red at the frontal cortex of the sheep brain. (scale=20 mm). The central panel shows electrophysiological recordings of spinal cord potentials (SCP) that were evoked through stimulation of deep brain structure (thalamus). An associated CT shows catheter position where the tip is circled in red. (scale=20 mm). The panel on the right shows stimulation of the spinal cord results in recorded compound muscle action potentials in surrounding back muscles. An x-ray scan shows catheter position inside the subarachnoid space around the thoracic spinal cord. (scale=50 mm). A schematic image of the sheep and positions of catheter electrode and neural stimulation are shown below the recorded data and associated scans.

FIG. 10 illustrates a schematic showing the synchronized stimulation of brain and spinal cord with the magnetoelectric powered implant, where cortical and ascending neural signals are sent between the two structures. Time locked recordings of simultaneous brain and spinal cord stimulations with surface needle electrodes showing resulting compound muscle action potentials (CMAPs) are shown on the right portion of the figure.

Referring now to FIG. 11, a schematic of an experimental data collection setup to validate wireless recording with the ECI is shown. The frontal cortex of the brain is first stimulated with a wireless ME implant through a catheter electrode and a central signal is then propagated to the spinal cord where a muscle contraction occurs and is recorded through intramuscular electrodes. The signal is sent wirelessly through magnetoelectric backscatter from the implant to the recording coil as shown and wirelessly recorded CMAP through ME backscatter from the intramuscular electrodes. Muscle activity recordings with increasing amplitude comparing stimulation threshold at Day 0 and at Day 30 in a sheep model. The histology from a sheep implanted with the ECI is shown in the lower portion of the figure. The animal was implanted and stimulated at day 0, stimulated again at day 30 and the device explanted, and the sheep was sacrificed one week later. (scale left=500 μm, middle=200 μm, right=200 μm).

FIG. 12 illustrates a three-dimensional reconstruction of the catheter electrode going through the craniocervical junction and navigating to frontal cortex of the brain (highlighted in blue) according to an exemplary embodiment of the present disclosure. FIG. 13 shows programmable voltage-controlled stimulation pulses generated by the magnetoelectric wireless implant in the upper portion of the figure. The lower portion of FIG. 13 shows a sample data uplink where light grey is the transmitter coil current, and dark grey represents the backscattered magnetic field. The upper portion of FIG. 14 illustrates stimulation with bipolar electrodes in the thoracic region of the spinal cord and recorded CMAPs, while the lower portion illustrates stimulation with bipolar electrodes in the frontal convexity of the brain and recorded MEPs on the hind legs of the sheep.

FIG. 15 provides a nine-pulse waterfall plot showing central activation with shifting latencies with first increasing stimulation amplitude from 0 mA to 8 mA and then decreasing back down to 0 mA. The color represents the max voltage reached on the trace as indicated in the bar graph to the right of the plot. Referring now to FIG. 16, a catheter recording from within the subarachnoid space surrounding the spinal cord where a D-wave is visible following the high frequency stimulation artifact, with an EKG also visible according to an exemplary embodiment of the present disclosure. FIG. 17 illustrates an EEG recording through a catheter electrode from the frontal convexity of the brain in the left portion of the figure, as well as fast fourier transform of the EEG signal to highlight the frequency components of the signal in the right portion of the figure. FIG. 18 illustrates a high-power image of lumbar epidural reactive vasculature from a sheep with mild lymphocytic and histiocytic inflammation with rare foreign body-type giant cells. FIG. 19 illustrates a cervical spinal cord histology in a survival sheep showing mild inflammation in subdural space in the left panel, and a histology of midbrain in the same survival sheep showing normal parenchyma and only minimal inflammation in leptomeninges in the right panel.

FIG. 20 illustrates measurements of spinal canal width taken from the MRIs of human patients. Data presented in the figure is the average of the anterior and posterior segments, with the black line measured at vertebral disc level while the gold line is measured at intervertebral disc level. FIG. 21 illustrates heart rate measurements from one sheep showing heart rate under anesthesia, after lumbar puncture, and during/after electrical stimulation through the subarachnoid space according to an exemplary embodiment of the present disclosure. The elevation of heart rate after electrical stimulation is likely a response to pain from stimulation of the dura. The left portion of FIG. 22 shows a recording from intrathecal space with ME stimulation post-euthanasia of the sheep according to an exemplary embodiment of the present disclosure. The top graph is a zoomed-in waveform marked with a star showing only stimulation artifacts. The right portion of the figures shows a recording from neck electrodes with ME stimulation post-euthanasia of the sheep according to an exemplary embodiment. The top graph is a zoomed-in waveform marked with a star showing only stimulation artifacts.

All of the devices and methods disclosed and claimed herein can be made and executed without undue experimentation in light of the present disclosure. While the devices and methods of this disclosure have been described in terms of preferred embodiments, it will be apparent to those of skill in the art that variations may be applied to the devices and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references are incorporated herein by reference.
ADDIN ZOTERO_BIBL {"uncited": [ ], "omitted": [ ], "custom": [ ]} CSL_BIBLIOGRAPHY 1. Deuschl, G. et al. A Randomized Trial of Deep-Brain Stimulation for Parkinson's Disease. N Engl J Med (2006).
2. Sinclair, C., Verrills, P. & Barnard, A. A review of spinal cord stimulation systems for chronic pain. J. Pain Res. Volume 9, 481-492 (2016).
3. Perlmutter, J. S. & Mink, J. W. DEEP BRAIN STIMULATION. (2006).
4. Holtzheimer, P. E. & Mayberg, H. S. Deep Brain Stimulation for Psychiatric Disorders. Annu. Rev. Neurosci. 34, 289-307 (2011).
5. Lebedev, M. A. & Nicolelis, M. A. L. Brain-machine interfaces: past, present and future. Trends Neurosci. 29, 536-546 (2006).
6. Erden, Y. J. & Brey, P. Neurotechnology and ethics guidelines for human enhancement: The case of the hippocampal cognitive prosthesis. Artif. Organs 47, 1235-1241 (2023).
7. Wagner, F. B. et al. Targeted neurotechnology restores walking in humans with spinal cord injury. Nature 563, 65-71 (2018).
8. Lange, M. et al. Underutilization of deep brain stimulation for Parkinson's disease? A survey on possible clinical reasons. Acta Neurochir. (Wien) 159, 771-778 (2017).
9. Kramer, D. R. et al. Best surgical practices: a stepwise approach to the University of Pennsylvania deep brain stimulation protocol. Neurosurg. Focus 29, E3 (2010).
10. Steinmetz, N. A. et al. Neuropixels 2.0: A miniaturized high-density probe for stable, long-term brain recordings. Science 372, cabf4588 (2021).
11. Simeral, J. D., Kim, S.-P., Black, M. J., Donoghue, J. P. & Hochberg, L. R. Neural control of cursor trajectory and click by a human with tetraplegia 1000 days after implant of an intracortical microelectrode array. J. Neural Eng. 8, 025027 (2011).
12. Oxley, T. J. Minimally invasive endovascular stent-electrode array for high-fidelity, chronic recordings of cortical neural activity. Nat Biotechnol 34, (2016).
13. Peter Mitchell, Peter Yoo, Sarah C. M Lee, & Bruce C. V. Campbell. Assessment of Safety of a Fully Implanted Endovascular Brain-Computer Interface for Severe Paraylsis in 4 Patients. *JAMA Neurol.* 80, (2023).

14. Zhang, A. et al. Ultraflexible endovascular probes for brain recording through micrometer-scale vasculature. *Science* 381, 306-312 (2023).

15. Fan, J. Z., Lopez-Rivera, V. & Sheth, S. A. Over the Horizon: The Present and Future of Endovascular Neural Recording and Stimulation. *Front. Neurosci.* 14, 432 (2020).

16. Wichmann, T. O., Damkier, H. H. & Pedersen, M. A Brief Overview of the Cerebrospinal Fluid System and Its Implications for Brain and Spinal Cord Diseases. *Front. Hum. Neurosci.* 15, 737217 (2022).

17. Aghaycv, K., Iqbal, S. M., Asghar, W., Shahmurzada, B. & Vrionis, F. D. Advances in CSF shunt devices and their assessment for the treatment of hydrocephalus. *Expert Rev. Med. Devices* 18, 865-873 (2021).

18. Singer, A. & Robinson, J. T. Wireless Power Delivery Techniques for Miniature Implantable Bioclectronics. *Adv. Healthc. Mater.* 10, 2100664 (2021).

19. Singer, A. Magnetoelectric materials for miniature, wireless neural stimulation at therapeutic frequencies. *Neuron* 107, (2020).

20. Chen, J. C. et al. A wireless millimetric magnetoelectric implant for the endovascular stimulation of peripheral nerves. *Nat. Biomed. Eng.* 6, 706-716 (2022).

21. Yu, Z. et al. Multisite bio-stimulating implants magnetoelectrically powered and individually programmed by a single transmitter. in 2021 *IEEE Custom Integrated Circuits Conference (CICC)* 1-2 (IEEE, Austin, TX, USA, 2021). doi: 10.1109/CICC51472.2021.9431457.

22. Yu, Z. et al. MagNI: A Magnetoelectrically Powered and Controlled Wireless Neurostimulating Implant. *IEEE Trans. Biomed. Circuits Syst.* 14, 1241-1252 (2020).

23. Sonmezoglu, S. Monitoring deep-tissue oxygenation with a millimeter-scale ultrasonic implant. *Nat Biotechnol* 39, (2021).

24. Piech, D. K. A wireless millimetre-scale implantable neural stimulator with ultrasonically powered bidirectional communication. *Nat Biomed Eng* 4, (2020).

25. Laiwalla, F. et al. A Distributed Wireless Network of Implantable Sub-mm Cortical Microstimulators for Brain-Computer Interfaces. in 2019 *41st Annual International Conference of the IEEE Engineering in Medicine and Biology Society (EMBC)* 6876-6879 (IEEE, Berlin, Germany, 2019). doi: 10.1109/EMBC.2019.8857217.

26. Shi, C. et al. Application of a sub-0.1-mm$^3$ implantable mote for in vivo real-time wireless temperature sensing. *Sci. Adv.* 7, cabf6312 (2021).

27. Agrawal, D. R. et al. Conformal phased surfaces for wireless powering of bioelectronic microdevices. *Nat. Biomed. Eng.* 1, 0043 (2017).

28. Ho, E. et al. *The Layer 7 Cortical Interface: A Scalable and Minimally Invasive Brain-Computer Interface Platform.* http://biorxiv.org/lookup/doi/10.1101/2022.01.02.474656 (2022) doi: 10.1101/2022.01.02.474656.

29. Khodagholy, D. et al. NeuroGrid: recording action potentials from the surface of the brain. *Nat. Neurosci.* 18, 310-315 (2015).

30. Woodington, B. J. et al. Electronics with shape actuation for minimally invasive spinal cord stimulation. *Sci. Adv.* 7, cabg7833 (2021).

31. Taghian, T. et al. A Safe and Reliable Technique for CNS Delivery of AAV Vectors in the Cisterna Magna. *Mol. Ther.* 28, 411-421 (2020).

32. Flotte, T. R. et al. AAV gene therapy for Tay-Sachs disease. *Nat. Med.* 28, 251-259 (2022).

33. Kandziora, F. et al. Comparison Between Sheep and Human Cervical Spines: An Anatomic, Radiographic, Bone Mineral Density, and Biomechanical Study. *Spine* 26, 1028-1037 (2001).

34. Wilke, H.-J., Kettler, A., Wenger, K. H. & Claes, L. E. Anatomy of the sheep spine and its comparison to the human spine. *Anat. Rec.* 247, 542-555 (1997).

35. Woods, J. E. et al. *Millimeter-Sized Battery-Free Epidural Cortical Stimulators.* http://medrxiv.org/lookup/doi/10.1101/2023.09.13.23295460 (2023) doi: 10.1101/2023.09.13.23295460.

36. Yu, Z. et al. Magnetoelectric backscatter communication for millimeter-sized wireless biomedical implants. in *Proceedings of the 28th Annual International Conference on Mobile Computing And Networking* 432-445 (ACM, Sydney NSW Australia, 2022). doi: 10.1145/3495243.3560541.

37. Alrashdan, F. T. et al. Wearable wireless power systems for 'ME-BIT' magnetoelectric-powered bio implants. *J. Neural Eng.* 18, 045011 (2021).

38. Rothwell, J. et al. Transcranial electrical stimulation of the motor cortex in man: further evidence for the site of activation. *J. Physiol.* 481, 243-250 (1994).

39. McPherson, J. G., Miller, R. R. & Perlmutter, S. I. Targeted, activity-dependent spinal stimulation produces long-lasting motor recovery in chronic cervical spinal cord injury. *Proc. Natl. Acad. Sci.* 112, 12193-12198 (2015).

40. Jackson, A. & Zimmermann, J. B. Neural interfaces for the brain and spinal cord-restoring motor function. *Nat. Rev. Neurol.* 8, 690-699 (2012).

41. Fanelli, A. & Ghezzi, D. Transient electronics: new opportunities for implantable neurotechnology. *Curr. Opin. Biotechnol.* 72, 22-28 (2021).

42. Parker, J. L., Karantonis, D. M., Single, P. S., Obradovic, M. & Cousins, M. J. Compound action potentials recorded in the human spinal cord during neurostimulation for pain relief. *Pain* 153, 593-601 (2012).

43. Baker, K. B. et al. Cerebellar deep brain stimulation for chronic post-stroke motor rehabilitation: a phase I trial. *Nat. Med.* 29, 2366-2374 (2023).

44. Blomstedt, P. & Hariz, M. I. Deep brain stimulation for movement disorders before DBS for movement disorders. *Parkinsonism Relat. Disord.* 16, 429-433 (2010).

45. Fettes, P., Schulze, L. & Downar, J. Cortico-Striatal-Thalamic Loop Circuits of the Orbitofrontal Cortex: Promising Therapeutic Targets in Psychiatric Illness. *Front. Syst. Neurosci.* 11, 25 (2017).

46. Goodman, W. K., Storch, E. A. & Sheth, S. A. Harmonizing the Neurobiology and Treatment of Obsessive-Compulsive Disorder. *Am. J. Psychiatry* 178, 17-29 (2021).

47. Loeb, G. E., Peck, R. A., Moore, W. H. & Hood, K. BION™ system for distributed neural prosthetic interfaces. *Med. Eng. Phys.* 23, 9-18 (2001).

48. A. Wakhloo et al. Image-guided endocisternal 3rd ventriculostomy (ETV). *J. of NeuroInterventional Surgery* 15, (2023).

49. Kim, W. et al. Magnetoelectrics enables large power delivery to mm-sized wireless bioelectronics. *J. Appl. Phys.* 134, 094103 (2023).

50. Wang, B. et al. Multichannel power electronics and magnetic nanoparticles for selective thermal magnetogenetics. *J. Neural Eng.* 19, 026015 (2022).

51. Gilbert, Z. et al. A review of neurophysiological effects and efficiency of waveform parameters in deep brain stimulation. *Clin. Neurophysiol.* 152, 93-111 (2023).

What is claimed is:

1. A cortical subarachnoid and intraventricular brain interface device comprising:

an implantable pulse generator; and a microelectrode catheter, wherein:

the microelectrode catheter comprises stimulating and recording electrodes; and the stimulating and recording electrodes are configured for implantation into a spinal and intracranial subarachnoid space or for implantation into ventricles of a brain.

2. The cortical subarachnoid and intraventricular brain interface device of claim 1 wherein the implantable pulse generator comprises a battery.

3. The cortical subarachnoid and intraventricular brain interface device of claim 1 wherein the microelectrode catheter is configured to be implanted either on the brain convexity or into the ventricular system of an animal.

4. The cortical subarachnoid and intraventricular brain interface device of claim 1 further comprising an external field transmitter for delivering data or energy to the implantable pulse generator.

5. The cortical subarachnoid and intraventricular brain interface device of claim 4 wherein the external field transmitter is configured to provide an alternating magnetic field powered by a field driver at 20 kHz-1 MHz, which powers a magnetoelectric film at its mechanical resonant frequency.

6. The cortical subarachnoid and intraventricular brain interface device of claim 1 wherein the implantable pulse generator is configured to generate stimulation amplitudes of at least 12.0 volts.

7. The cortical subarachnoid and intraventricular brain interface device of claim 1 wherein the implantable pulse generator is configured to generate a pulse width of approximately 250 μs.

8. The cortical subarachnoid and intraventricular brain interface device of claim 1 further comprising a wireless communication device.

9. The cortical subarachnoid and intraventricular brain interface device of claim 8 wherein the wireless communication device comprises a coil.

10. The cortical subarachnoid and intraventricular brain interface device of claim 8 wherein the wireless communication device is configured to:

transmit wireless signals to the implantable pulse generator; and receive wireless signals from the implantable pulse generator.

11. The cortical subarachnoid and intraventricular brain interface device of claim 8 wherein the wireless communication device is configured to communicate with the implantable pulse generator via a magnetoelectric backscatter protocol.

12. The cortical subarachnoid and intraventricular brain interface device of claim 1 wherein the implantable pulse generator comprises a magnetoelectric film.

13. The cortical subarachnoid and intraventricular brain interface device of claim 1 wherein the implantable pulse generator comprises a printed circuit board.

14. A method of implanting a cortical subarachnoid and intraventricular brain interface device, the method comprising:

performing a lumbar puncture to access spinal subarachnoid space;

advancing a microelectrode catheter through the spinal subarachnoid space;

implanting one or more stimulating electrodes and recording electrodes into a spinal or intracranial subarachnoid space or into ventricles of a brain of a subject;

implanting an implantable pulse generator into the subject;

generating a stimulation signal via the implantable pulse generator; and recording a response signal from the subject via the one or more recording electrodes.

15. The method of claim 14 further comprising transmitting the response signal via a magnetoelectric backscatter protocol.

16. The method of claim 14 wherein the implantable pulse generator comprises a magnetoelectric film.

* * * * *